US010004838B2

United States Patent
Gerber et al.

(10) Patent No.: US 10,004,838 B2
(45) Date of Patent: Jun. 26, 2018

(54) RESERVE ZIRCONIUM PHOSPHATE MODULE FOR USE IN SORBENT DIALYSIS

(71) Applicant: Medtronic, Inc., Minneapolis, MN (US)

(72) Inventors: Martin T. Gerber, Maple Grove, MN (US); Christopher M. Hobot, Tonka Bay, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 547 days.

(21) Appl. No.: 14/645,389

(22) Filed: Mar. 11, 2015

(65) Prior Publication Data
US 2015/0367057 A1 Dec. 24, 2015

Related U.S. Application Data

(60) Provisional application No. 62/016,606, filed on Jun. 24, 2014.

(51) Int. Cl.
| | |
|---|---|
| *A61M 1/16* | (2006.01) |
| *B01D 61/30* | (2006.01) |
| *B01D 61/32* | (2006.01) |
| *B01D 24/46* | (2006.01) |

(52) U.S. Cl.
CPC ........... *A61M 1/1696* (2013.01); *B01D 61/30* (2013.01); *B01D 61/32* (2013.01); *A61M 2205/18* (2013.01); *A61M 2205/33* (2013.01)

(58) Field of Classification Search
CPC .... A61M 1/16; A61M 1/1601; A61M 1/1656; A61M 1/1668; A61M 1/1694; A61M 1/1696; A61M 1/287; A61M 2205/33; B01D 61/24; B01D 61/243; B01D 61/28; B01D 61/30; B01D 61/32; B01D 24/46;
(Continued)

(56) References Cited

U.S. PATENT DOCUMENTS

| | | | |
|---|---|---|---|
| 3,669,880 A | 6/1972 | Marantz | |
| 3,884,808 A | 5/1975 | Scott | |
| 5,284,470 A | 2/1994 | Beltz | |

(Continued)

FOREIGN PATENT DOCUMENTS

| | | |
|---|---|---|
| CN | 104936633 | 9/2015 |
| WO | 2008075951 A1 | 6/2008 |

(Continued)

OTHER PUBLICATIONS

PCT/US2015/020046 International Search Report and Written Opinion dated Jun. 29, 2015.

(Continued)

*Primary Examiner* — Joseph Drodge
(74) *Attorney, Agent, or Firm* — Kenneth Collier; Roger Hahn

(57) ABSTRACT

A reserve zirconium phosphate module for continuing dialysis in the event the capacity of the original zirconium phosphate module is exceeded. The sorbent cartridge can have a sensor for detecting when the capacity of the zirconium phosphate material has been exceeded, and a valve assembly for diverting the flow of spent dialysate into the reserve module when needed. Any of the modules of the sorbent cartridge can be reusable and the sorbent materials therein recharged.

22 Claims, 18 Drawing Sheets

(58) Field of Classification Search
CPC .... B01J 20/02; B01J 20/0203; B01J 20/0211;
B01J 20/30; B01J 20/34; G01N 33/0054
USPC ....... 210/85, 96.1, 96.2, 264, 321.6, 321.71,
210/645, 646, 739, 670, 677, 678, 263,
210/269; 604/5.01, 6.01, 6.09, 25, 65,
604/67; 436/106, 108, 113; 502/20
See application file for complete search history.

(56) References Cited

U.S. PATENT DOCUMENTS

| | | | |
|---|---|---|---|
| 5,770,086 | A | 6/1998 | Indriksons |
| 5,849,179 | A | 12/1998 | Emerson et al. |
| 5,944,684 | A | 8/1999 | Roberts |
| 6,572,769 | B2 | 6/2003 | Rajan |
| 6,579,460 | B1 | 6/2003 | Willis |
| 6,960,179 | B2 | 11/2005 | Gura |
| 7,776,210 | B2 | 8/2010 | Rosenbaum |
| 7,947,179 | B2 | 5/2011 | Rosenbaum |
| 8,096,969 | B2 | 1/2012 | Roberts |
| 8,777,892 | B2 | 7/2014 | Sandford |
| 9,382,184 | B2 * | 7/2016 | Lange ............... C07C 51/265 |
| 9,707,328 | B2 * | 7/2017 | Pudil ................ B01J 39/10 |
| 9,713,666 | B2 * | 7/2017 | Pudil ................ A61M 1/14 |
| 2001/0007931 | A1 | 7/2001 | Blatter |
| 2002/0112609 | A1 | 8/2002 | Wong |
| 2002/0117436 | A1 | 8/2002 | Rajan |
| 2003/0097086 | A1 | 5/2003 | Gura |
| 2003/0113931 | A1 | 6/2003 | Pan et al. |
| 2003/0114787 | A1 | 6/2003 | Gura |
| 2004/0168963 | A1 | 9/2004 | King |
| 2004/0257409 | A1 | 12/2004 | Cheok |
| 2005/0101901 | A1 | 5/2005 | Gura |
| 2005/0148923 | A1 * | 7/2005 | Sternby ............. A61B 5/0275 604/4.01 |
| 2005/0209563 | A1 * | 9/2005 | Hopping ............ A61M 1/28 604/151 |
| 2005/0274658 | A1 | 12/2005 | Rosenbaum et al. |
| 2007/0003762 | A1 * | 1/2007 | Withiam ............ B01D 53/02 428/403 |
| 2007/0020166 | A1 * | 1/2007 | Withiam ............ C01B 33/143 423/339 |
| 2008/0051696 | A1 | 2/2008 | Curtin |
| 2008/0217245 | A1 | 9/2008 | Rambod |
| 2009/0266358 | A1 | 10/2009 | Sacristan Rock |
| 2010/0101195 | A1 | 4/2010 | Clements |
| 2010/0114012 | A1 * | 5/2010 | Sandford ........... A61M 1/1696 604/28 |
| 2010/0213127 | A1 * | 8/2010 | Castellarnau ....... A61M 1/16 210/647 |
| 2010/0252490 | A1 * | 10/2010 | Fulkerson ........... A61M 1/1656 210/96.2 |
| 2010/0314314 | A1 | 12/2010 | Ding |
| 2010/0326911 | A1 * | 12/2010 | Rosenbaum ........ A61M 1/1696 210/638 |
| 2011/0017665 | A1 | 1/2011 | Updyke |
| 2011/0315611 | A1 * | 12/2011 | Fulkerson ........... A61M 1/3639 210/96.2 |
| 2013/0030356 | A1 * | 1/2013 | Ding .................. A61M 1/1696 604/28 |
| 2013/0199998 | A1 | 8/2013 | Kelly et al. |
| 2014/0138294 | A1 | 5/2014 | Fulkerson |
| 2014/0148538 | A1 * | 5/2014 | Gane ................. C09C 1/021 524/247 |
| 2014/0217028 | A1 | 8/2014 | Pudil |
| 2014/0251908 | A1 | 9/2014 | Ding |
| 2014/0336568 | A1 * | 11/2014 | Wong ................ A61M 1/1696 604/29 |
| 2015/0144539 | A1 | 5/2015 | Pudil |
| 2015/0144542 | A1 | 5/2015 | Pudil |
| 2015/0157960 | A1 | 6/2015 | Pudil |
| 2015/0238673 | A1 | 8/2015 | Gerber |

FOREIGN PATENT DOCUMENTS

| | | |
|---|---|---|
| WO | 2010141949 | 12/2010 |
| WO | 2013028809 | 2/2013 |
| WO | WO2013028809 A2 | 2/2013 |
| WO | 2013101888 | 7/2013 |

OTHER PUBLICATIONS

PCT/US15/18587 International Preliminary Report on Patentability dated Jun. 6, 2016.
European Search Report for App. No. 15751391.2 dated Aug. 4, 2017.
European Search Report and supplementary Search Report for App. No. 14865374.4 dated Jun. 12, 2017.
Office Action for Chinese Application No. 2015/80009562.5 dated Jul. 3, 2017.
International Preliminary Report on Patentability for Application No. PCT/US2015/032492 dated Jun. 30, 2017.
International Preliminary Report on Patentability for Application No. PCT/US2015/016273 dated Feb. 19, 2016.
European Search Report for 15812559.1 date of completion is Jan. 26, 2018 (2 pages).
International Search Report for PCT/US2015/020046 date of completion is Jun. 29, 2015 (3 pages).

* cited by examiner

RESERVE ZIRCONIUM PHOSPHATE MODULE FOR USE IN SORBENT DIALYSIS

FIELD OF THE INVENTION

The invention relates to a reserve zirconium phosphate module for use in sorbent dialysis to allow dialysis to continue in the event of ammonia breakthrough.

BACKGROUND

Zirconium Phosphate (ZrP) is used during sorbent dialysis to absorb ammonium ions generated by the reaction of urease breaking down urea in dialyzed blood. The ZrP layer is oftentimes provided as a specific layer in a sorbent cartridge used during dialysis. However, urease is generally not expended before ZrP is exhausted during dialysis. As such, if a patient has a large amount of urea in the blood, which generates a large amount of ammonia from urease, the ZrP layer may not be able to adsorb all the ammonia generated by the urea. In that case, a sorbent cartridge's capacity to adsorb ammonia has been reached resulting in so-called "ammonia breakthrough." Ammonia may then enter the dialysate fluid, which is returned to the patient. Because ammonia is toxic, dialysis must be halted and the cartridge replaced.

In order to avoid ammonia breakthrough during therapy, oftentimes more zirconium phosphate is provided than is normally necessary, thereby ensuring that almost all patients can receive therapy without ammonia breakthrough. This provides enough zirconium phosphate for the majority of patients, but increases costs and waste by using more of the zirconium phosphate than is necessary.

Known dialysate fluid circulation systems and apparatuses have systems in place to halt dialysis in the event of ammonia breakthrough. In other systems, additional zirconium phosphate may be added in order to continue dialysis. An alternative to stopping dialysis involves bypassing a module containing urease, and thereby stopping the process of creating ammonia. However, although other toxins can continue to be removed from the patient, urea is no longer removed from the dialysate. In order to minimize the frequency of ammonia breakthrough, some sorbent cartridges use more zirconium phosphate than is necessary for most patients. This allows dialysis to continue as normal for larger or more uremic patients. However, providing more zirconium phosphate than is necessary for most patients results in increased costs and waste along with larger and more cumbersome cartridges. Customizing sorbent cartridges for larger or more uremic patients likewise increases costs. Alternatively, expensive sorbent materials have been used to remove ammonia from spent dialysate. However, the systems do not provide for recharging some or all of the components of a sorbent cartridge that would allow reuse of specific components to enable lower long-term costs for operating such systems.

As such, there is a need for removing urea without halting dialysis or risking harm to a patient in the event of ammonia breakthrough. There is also a need for improving the effectiveness and efficiency of a sorbent cartridge by reducing the amount of expensive, rate-limiting sorbent materials used during dialysis. There is a need for avoiding ammonia breakthrough during therapy without providing more zirconium phosphate than is required while ensuring that almost all patients can receive therapy without ammonia breakthrough. There is a need for avoiding increased costs and waste by avoiding using more of the zirconium phosphate than is necessary for safe dialysis. There is a further need for a sorbent cartridge and related systems and methods having a reserve module containing a sorbent material capable of removing ammonia from dialysate so that dialysis can continue in the event of ammonia breakthrough. There is a need for a sorbent cartridge providing for the use of a reserve sorbent module to allow normal operation with a smaller amount of sorbent material, while at the same time ensuring that ammonia breakthrough does not occur.

SUMMARY OF THE INVENTION

The first aspect of the invention relates to a dialysate regeneration system. In any embodiment of the first aspect of the invention, the dialysate regeneration system can comprise a first compartment having at least one sorbent material wherein the at least one sorbent material is capable of removing ammonia or ammonium ions from a fluid, and a second compartment having at least one sorbent material capable of removing ammonia or ammonium ions from a fluid; the first and second compartment can be in fluid communication controlled by one or more valves positioned to direct fluid into either the first compartment or the second compartment based on detection of ammonia breakthrough.

In any embodiment of the first aspect of the invention, the dialysate regeneration system can comprise an ammonia detector positioned in a fluid flow path such that the ammonia detector can detect ammonia or ammonium ions in the fluid after leaving the first or second compartment.

In any embodiment of the first aspect of the invention, the dialysate regeneration system can comprise one or more additional compartments positioned before or after the first compartment.

In any embodiment of the first aspect of the invention, the one or more compartment can contain at least one sorbent material.

In any embodiment of the first aspect of the invention, the dialysate regeneration system can comprise a processor configured to receive data from the ammonia detector.

In any embodiment of the first aspect of the invention, the dialysate regeneration system can comprise an alarm mechanism such that if the ammonia detector detects ammonia or ammonium ions in a higher concentration than a pre-set level, the system provides an alert.

In any embodiment of the first aspect of the invention, the processor can automatically switch the one or more valves to direct flow into the second compartment if the ammonia detector detects ammonia or ammonium ions in a higher concentration than a pre-set value.

In any embodiment of the first aspect of the invention, the processor can automatically stop the dialysis system if the ammonia detector detects ammonia or ammonium ions in a higher concentration than a pre-set value and there is less than a pre-set amount of time remaining in a dialysis session.

In any embodiment of the first aspect of the invention, the at least one sorbent material in the first or second compartment can comprise zirconium phosphate.

In any embodiment of the first aspect of the invention, the dialysate regeneration system can further comprise a recharger fluidly connected to the one or more valves such that fluid may be directed from the recharger into the first compartment.

In any embodiment of the first aspect of the invention, the dialysate regeneration system can comprise a recharger fluidly connected to the one or more valves such that fluid can be directed from the recharger into the second compartment.

In any embodiment of the first aspect of the invention, the dialysate regeneration system can comprise a bypass line fluidly connected to the one or more valves such that the one or more valves can direct fluid into the bypass line and away from either the first or second compartment.

In any embodiment of the first aspect of the invention, the ammonia detector can be positioned in the fluid flow path such that the ammonia detector can also detect ammonia or ammonium ions in the fluid after leaving the second compartment.

In any embodiment of the first aspect of the invention, the dialysate regeneration system can comprise a second ammonia detector positioned in a fluid flow path such that the second ammonia detector can detect ammonia or ammonium ions in the fluid leaving the second compartment.

In any embodiment of the first aspect of the invention, any one of the additional compartments can contain a sorbent material capable of converting urea to ammonia or ammonium ions.

In any embodiment of the first aspect of the invention, the dialysate regeneration system can comprise a bypass line fluidly connected to a second set of one or more valves positioned before the additional compartment such that fluid can be caused to bypass the additional compartment.

In any embodiment of the first aspect of the invention, the second set of one or more valves can automatically cause fluid to bypass the additional compartment when ammonia or ammonium ions are detected in a concentration higher than a pre-set value in the fluid leaving both the first compartment and the second compartment.

In any embodiment of the first aspect of the invention, the sorbent cartridge can be in a controlled compliant flow path.

In any embodiment of the first aspect of the invention, the second compartment can contain between 50 and 500 grams of zirconium phosphate.

In any embodiment of the first aspect of the invention, the second compartment can contain between 100 and 1500 grams of zirconium phosphate.

In any embodiment of the first aspect of the invention, the second compartment can contain zirconium phosphate with an ammonium binding capacity for any range contained between 0.5 and 5.0 mmol/gram, and specifically between any of 0.5 and 1.0 mmol/gram, 1.0 and 1.5 mmol/gram, 1.5 and 2.0 mmol/gram, 2.0 and 2.5 mmol/gram, 2.5 and 3.0 mmol/gram, 3.0 and 3.5 mmol/gram, 3.5 and 4.0 mmol/gram, 4.0 and 4.5 mmol/gram, 4.5 and 5.0 mmol/gram, 1.5 and 3.0 mmol/gram, 2.5 and 3.0 mmol/gram, 2.5 and 4.5 mmol/gram, 0.5 and 3.0 mmol/gram, 0.5 and 3.5 mmol/gram, 1.0 and 4.5 mmol/gram, 1.5 and 3.5 mmol/gram, or 2.0 and 5.0 mmol/gram.

In any embodiment of the first aspect of the invention, the valves of the dialysate regeneration system can be any of two-way, three-way or four-way valves, or combinations thereof.

Any of the features disclosed as being part of the first aspect of the invention can be included in the first aspect of the invention, either alone or in combination.

The second aspect of the invention relates to a dialysate regeneration system comprising a sorbent cartridge comprising at least a first compartment and a second compartment positioned in series. The first compartment can have at least one sorbent material capable of removing ammonia or ammonium ions from a fluid. The second compartment can have at least one sorbent material capable of removing ammonia or ammonium ions from a fluid. The first compartment and the second compartment can be in fluid communication controlled by one or more valves positioned on a connector after the first compartment.

In any embodiment of the second aspect of the invention, the dialysate regeneration system can further comprise a bypass line connected to the one or more valves positioned on a connector after the first compartment such that fluid may be directed into the bypass line and around the second compartment; wherein the one or more valves are initially set to direct fluid into the bypass line and around the second compartment. The one or more valves can be initially set to direct fluid into the bypass line and around the second compartment.

In any embodiment of the second aspect of the invention, the dialysate regeneration system can further comprise an ammonia detector positioned in a fluid flow path after the first compartment such that the ammonia detector can detect ammonia or ammonium ions in fluid leaving the first compartment.

In any embodiment of the second aspect of the invention, the system can further comprise a processor configured to receive data from the ammonia detector.

In any embodiment of the second aspect of the invention, the processor can cause the one or more valves to switch, such that fluid is directed into the second compartment, when the ammonia detector detects ammonia or ammonium ions in the fluid leaving the first compartment.

In any embodiment of the second aspect of the invention, the first compartment can further comprise a sorbent material capable of converting urea to ammonia or ammonium ions.

In any embodiment of the second aspect of the invention, the dialysate regeneration system can further comprise an additional compartment positioned before the first or second compartments. The additional compartment can comprise at least one sorbent material that can convert urea to ammonia or ammonium ions.

Any of the features disclosed as being part of the second aspect of the invention can be included in the second aspect of the invention, either alone or in combination.

The third aspect of the invention is directed towards a method. In any embodiment of the third aspect of the invention, the method can comprise determining an amount of ammonia leaving a first compartment capable of removing ammonia or ammonium ions from a fluid using an ammonium sensor, and diverting flow from the first compartment to a second compartment capable of removing ammonia or ammonium ions from a fluid if ammonia breakthrough is detected.

In any embodiment of the third aspect of the invention, the method can comprise the step of switching one or more valves to direct fluid into the second compartment when the ammonia detector detects ammonia or ammonium ions in the fluid leaving the first compartment.

In any embodiment of the third aspect of the invention, the method can comprise the step of bypassing the first compartment using the one or more valves such that fluid may be directed into a bypass line and around the second compartment.

Any of the features disclosed as being part of the third aspect of the invention can be included in the third aspect of the invention, either alone or in combination.

DETAILED DESCRIPTION OF THE INVENTION

Figure 1:
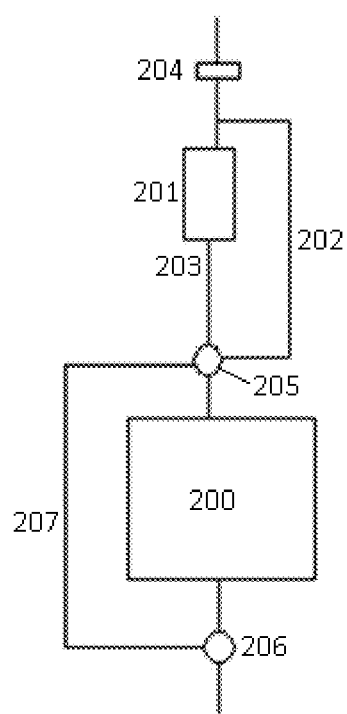
FIG. 1 shows a sorbent cartridge with zirconium phosphate in a first compartment, a zirconium phosphate reserve compartment and an ammonia detector.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

An "additional compartment" can be any one of the sorbent layers.

An "alert" may include any means of notification, such as a sound, light, message, etc. to make the user or health care provider aware that ammonia or ammonium ions have been detected at a concentration higher than a pre-set level.

"Ammonium binding capacity" refers to the amount of ammonium that can be bound by a given amount of sorbent material. Ammonium binding capacity can be expressed in the units mmol/gram, wherein 1 mmol/gram refers to 1 mmol of ammonium ions capable of being bound by 1 gram of the sorbent material.

"Ammonia breakthrough" is a condition occurring during sorbent dialysis wherein an ammonia adsorbing layer such as zirconium phosphate can no longer adsorb ammonia causing the unwanted release of ammonia into the dialysate.

"Ammonia detector" refers to any apparatus that is capable of detecting the presence of or concentration of ammonia or ammonium ions in a fluid. Detectors may be chemical or electrochemical, or photoionization detectors may be used, as well as any other ammonia detection means known in the art.

"Bypass line" refers to a line, connected to the main line, through which fluid or gas may alternatively flow.

The term "cartridge" refers to any container designed to contain a powder, fluid, or gas made for ready connection to a device, structure, system, flow path or mechanism. The container can have one or more compartments. Instead of compartments, the container can also be comprised of a system of two or more modules connected together to form the cartridge wherein the two or more modules once formed can be connected to a device, structure, system, flow path or mechanism.

A "compartment" means a part or a space designated, defined, marked or partitioned off from a structure. For example, a urease compartment in a sorbent cartridge is space defined within the sorbent cartridge containing urease. Optionally, the compartment can be in selected fluid communication with other compartments or modules of the sorbent system. The compartment can be physically separated or marked off without a physical barrier.

The term "comprising" includes, but is not limited to, whatever follows the word "comprising." Thus, use of the term indicates that the listed elements are required or mandatory but that other elements are optional and may or may not be present.

A "connector" as used herein forms a fluid connection between two components wherein fluid or gas can flow from one component, through the connector, to another component. The connector provides for a fluid connection in its broadest sense and can include any type of tubing, fluid or gas passageway, or conduit between any one or more components of the invention.

The term "consisting of" includes and is limited to whatever follows the phrase "consisting of." Thus, the phrase indicates that the limited elements are required or mandatory and that no other elements may be present. The term "consisting essentially of" includes whatever follows the term "consisting essentially of" and additional elements, structures, acts or features that do not affect the basic operation of the apparatus, structure or method described.

The term "container" as used herein is a receptacle that may be flexible or inflexible for holding any fluid or solid, such as for example a spent dialysate fluid, or a sodium chloride or sodium bicarbonate solution or solid, or the like.

The terms "controlled compliance" and "controlled compliant" describe the ability to actively control the transfer of fluid volume into or out of a compartment, flow path or circuit. In certain embodiments, the variable volume of fluid in a dialysate circuit or controlled compliant flow path expands and contracts via the control of one or more pumps in conjunction with one or more reservoirs. The volume of fluid in the system is generally constant (unless additional fluids are added to a reservoir from outside of the system) once the system is in operation if patient fluid volume(s), flow paths, and reservoirs are considered part of the total volume of the system (each individual volume may sometimes be referred to as a fluid compartment). The attached reservoirs allow the system to adjust the patient fluid volume by withdrawing fluid and storing the desired amount in an attached control reservoir and/or by providing purified and/or rebalanced fluids to the patient and optionally removing waste products. The terms "controlled compliance" and "controlled compliant" are not to be confused with the term "non-compliant volume," which simply refers to a vessel, conduit, container, flow path, conditioning flow path or cartridge that resists the introduction of a volume of fluid after air has been removed from a defined space such as a vessel, conduit, container, flow path, conditioning flow path or cartridge. In one embodiment, the controlled compliant system can move fluids bi-directionally. In certain cases, the bi-directional fluid movement can be across a semi-permeable membrane either inside or outside a dialyzer. The bi-directional fluid flow can also occur across, through, or between vessels, conduits, containers, flow paths, conditioning flow paths or cartridges of the invention in selected modes of operation. The term "moving fluid bi-directionally" as used in connection with a barrier, such as a semi-permeable membrane, refers to the ability to move fluid across the barrier in either direction. "Moving fluid bi-directionally" also can apply to the ability to move fluid in both directions in the flow path or between a flow path and reservoir in a controlled compliant system.

The terms "controlled compliant flow path," "controlled compliant dialysate flow path" and "controlled compliant solution flow path" refer to flow paths operating within a controlled compliant system having the characteristic of controlled compliance, or of being controlled compliant as defined herein.

A "controller," "control unit," "processor," or "microprocessor" is a device which monitors and affects the operational conditions of a given system. The operational conditions are typically referred to as output variables of the system wherein the output variables can be affected by adjusting certain input variables.

The term "detachable" or "detached" relates to any component of the present invention that can be separated from a system, module, cartridge or any component of the invention. "Detachable" can also refer to a component that can be taken out of a larger system with minimal time or effort. In certain instances, the components can be detached with minimal time or effort, but in other instances can require additional effort. The detached component can be optionally reattached to the system, module, cartridge or other component. A detachable module can often be part of a reusable module.

"Dialysate" is the fluid that passes through the dialyzer on the side of the dialysis membrane that is opposite to the fluid (e.g. blood) that is being dialyzed.

A "dialysate regeneration system" is a system having first and second compartments having at least one sorbent material in each compartment that is capable of removing ammonia or ammonium ions from a fluid. The first and second compartments are in fluid communication controlled by one or more valves positioned to direct fluid into either the first compartment or the second compartment based on detection of ammonia breakthrough.

"Diverting flow" describes a process of redirecting flow of spent dialysate or other fluid from one intended path leading to one compartment to an alternate path leading to another compartment. Flow may be diverted by opening or closing valves, and may be done manually or automatically in response to signals received from sensors detecting ammonia breakthrough.

A "first compartment" defines an internal space holding sorbent material. A "second compartment" defines a separate internal space from the first compartment also holding sorbent material.

"Flow" refers to the movement of a fluid or gas.

A "flow sensing apparatus" or "flow measuring apparatus" is an apparatus capable of measuring the flow of fluid or gas within a specific area.

A "fluid" is a liquid substance optionally having a combination of gas and liquid phases in the fluid. Notably, a liquid, as used herein, can therefore also have a mixture of gas and liquid phases of matter.

The term "fluid communication" refers to the ability of fluid or gas to move from one component or compartment to another within a system or the state of being connected, such that fluid or gas can move by pressure differences from one portion connected to another portion.

The term "fluidly connectable" refers to the ability of providing for the passage of fluid or gas from one point to another point. The two points can be within or between any one or more of compartments, modules, systems, components, and rechargers, all of any type.

The term "in-line" refers to a state in which a module or set of modules is fluidly connected to a dialysis machine, dialysis flow path or dialysis circuit. Dialysis can be on-going, paused or stopped during the in-line state wherein in-line only refers to the state of the modules being fluidly connected to the dialysis machine, dialysis flow path or dialysis circuit.

"Module" refers to a discreet component of a system. Each of the modules can be fitted to each other to form a system of two or more modules. Once fitted together, the modules can be in fluid connection and resist inadvertent disconnection. A single module can represent a cartridge to be fitted to a device or mechanism if the module is designed to contain all the necessary components for an intended purpose such as a sorbent for use in dialysis. In such a case, the module can be comprised of one or more compartments within the module. Alternatively, two or more modules can form a cartridge to be fitted to a device or mechanism wherein each module individually carries separate components but only when connected together contain in summation all the necessary components for an intended purpose such as a sorbent for use in dialysis. A module can be referred to as a "first module," "second module," "third module," etc. to refer to any number of modules. It will be understood that the designation of "first," "second," "third," etc. does not refer to the respective placement of the module in the direction of fluid or gas flow, and merely serves to distinguish one module from another unless otherwise indicated.

The term "off-line" refers to a state in which a module or set of modules is fluidly disconnected from a dialysis machine, dialysis flow path or dialysis circuit. Dialysis can be on-going, paused or stopped during the off-line state wherein off-line only refers to the state of the modules being fluidly disconnected from the dialysis machine, dialysis flow path or dialysis circuit. The off-line state can also include a process whereby the module or set of modules is being recharged as defined herein.

An "operational line" or "line" is a passageway, conduit or connector that directs fluid or gas in a path used while the system is in operation.

The terms "pathway," "conveyance pathway," "fluid flow path," and "flow path" refer to the route through which a fluid, such as dialysate or blood, travels.

A "photocell" is a sensor capable of measuring light or other electromagnetic radiation.

A "photodetector" is a sensor capable of detecting the intensity or wavelength of light.

A "pre-set level" is a measurable concentration of ammonia or ammonium ions, detection beyond which by an ammonia detector results in an alert being issued.

A "recharger" is a component that is capable of recharging spent sorbent material to or near its original state. A recharger may be part of the dialysis system or may be separate from the rest of the system. If the recharger is separate from the rest of the dialysis system, the term may include a separate facility where the spent sorbent material is sent to be returned to, or near, its original state. A "recharger connector" or "recharger node" is a connector that fluidly connects a recharger to another component.

"Recharging" refers to the process of treating spent sorbent material to restore the functional capacity of the sorbent material, so as to put the sorbent material back into a condition for reuse or for use in a new dialysis session. In some instances, the total mass, weight and/or amount of "rechargeable" sorbent materials remain the same. In other embodiments, the total mass, weight and/or amount of "rechargeable" sorbent materials may change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged."

A "sensor" is a component capable of determining the states of one or more variables in a system.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular design wherein the sorbent materials are dispersed across at least two different modules, which can be connected to form a unitary body. Once the at least two modules are connected together, the connected modules can be referred to as a sorbent cartridge, which can be fitted to a device or mechanism. When a single module contains all the sorbent materials necessary for performing dialysis, the single module can be referred to as a sorbent cartridge.

"Sorbent materials" are materials capable of removing specific solutes from solution, such as urea or urea byproducts.

"Spent dialysate" is a dialysate contacted with blood through a dialysis membrane and containing one or more impurities, or waste species, or waste substance, such as urea.

The term "substantially inflexible volume" refers to a three-dimensional space within a vessel or container that can accommodate a maximum amount of non-compressible fluid and resists the addition of any volume of fluid above the maximum amount. The presence of a volume of fluid less than the maximum amount will fail to completely fill the vessel or container. Once a substantially inflexible volume has been filled with a fluid, removal of fluid from that volume will create a negative pressure that resists fluid removal unless fluid is added and removed simultaneously at substantially equal rates. Those skilled in the art will recognize that a minimal amount of expansion or contraction of the vessel or container can occur in a substantially inflexible volume; however, addition or subtraction of a significant volume of fluid over the maximum or minimum will be resisted.

A "valve" is a device capable of directing the flow of fluid or gas by opening, closing or obstructing one or more pathways to allow the fluid or gas to travel in a particular path. The valves can be two-way, three-way or four-way valves. One or more valves configured to accomplish a desired flow can be configured into a "valve assembly."

A "wash line" is a line that directs fluid between a recharger and a module.

Zirconium Phosphate Reserve Module

The first, second and third aspects of the invention avoid ammonia breakthrough by use of a Zirconium Phosphate (ZrP) reserve. When the system detects ammonia breakthrough, the system can automatically switch the flow of spent dialysate into the ZrP reserve. The reserve can contain enough ZrP to allow dialysis to continue, while ensuring that ammonia created by passing the spent dialysate through the urease does not enter the patient's blood.

In any embodiment of the first, second, and third aspects of the invention, the normal ZrP compartment 200 and the ZrP reserve 201 can be positioned in series as shown in FIG. 1. During normal operation, fluid can pass through ZrP compartment 200. Fluid leaving ZrP compartment 200 can then be directed into bypass line 202 by valve 205, bypassing the reserve line 203 and ZrP reserve 201. If the capacity of the normal ZrP compartment 200 is exceeded, as detected by ammonia detector 204, then the valve 205 can be switched to direct fluid into reserve line 203 and ZrP reserve compartment 201, allowing dialysis to continue. Optionally second bypass line 207 can be included so that if the capacity of ZrP compartment 200 is exceeded second valve 206 can be switched so as to direct flow into second bypass line 207 and around the normal ZrP compartment 200. In any embodiment of the first, second, or third aspects of the invention, fluid can continue to flow through normal ZrP compartment 200, even after the capacity has been exceeded. In any embodiment of the first, second, or third aspects of the invention, other sorbent materials, such as activated carbon, hydrous zirconium oxide, and alumina and urease can be located in a separate compartment (not shown), placed before the normal ZrP compartment 200 in the fluid flow path. Rechargers (not shown) can be connected to ZrP compartment 200 and ZrP reserve 201, respectively, so that either compartment can be recharged. In any embodiment of the first, second, or third aspects of the invention, ZrP compartment 200 and ZrP reserve compartment 201 may be detachable from the sorbent cartridge (not shown) to facilitate recharging or replacing of the compartments.

The ability to remove urea can be limited by the capacity of ZrP disposed in a layer, module, or component. The ZrP can exchange ammonium ions ($NH_4^+$). Different layers of ZrP can be constructed to remove an amount of ammonium ions ($NH_4^+$) or ammonia as measured by an ammonium binding capacity of average capacity for $NH_4^+$ adsorption. Depending on the source of the ZrP, the manufacturing process, and the like, the ZrP may have varying ranges of ammonium binding capacity. It will be understood that the first, second, or third aspects of the invention contemplate any range of ammonium binding capacity of commercially available ZrP in any form suitable for use in dialysis.

Figure 2:
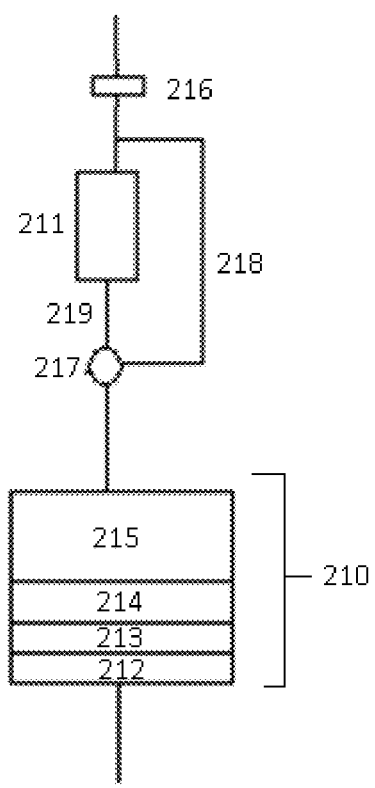
FIG. 2 shows a sorbent cartridge with activated carbon, alumina, urease, hydrous zirconium oxide and zirconium phosphate in the first compartment and a zirconium phosphate reserve compartment.

In any embodiment of the first, second, or third aspects of the invention, the ZrP in the ZrP module and the ZrP reserve module can have an ammonium binding capacity of between 0.1 and 5 mmol/gram. It will be expressly understood that the range 0.1 and 5 mmol/gram includes any range contained therein such as a range of 0.1 to 4.9 mmol/gram, 4.8 to 4.9 mmol/gram, 0.1 to 0.2 mmol/gram, or any other two points within the range. In any embodiment of the first, second, or third aspects of the invention, the zirconium phosphate can have an ammonium binding capacity of between 0.5 and 1.0 mmol/gram, between 1.0 and 1.5 mmol/gram, between 1.5 and 2.0 mmol/gram, between 2.0 and 2.5 mmol/gram, between 2.5 and 3.0 mmol/gram, between 3.0 and 3.5 mmol/gram, between 3.5 and 4.0 mmol/gram, between 4.0 and 4.5 mmol/gram, or between 4.5 and 5.0 mmol/gram. In any embodiment of the first, second, or third aspects of the invention, as shown in FIG. 2, a first compartment 210 can contain activated carbon 212, hydrous zirconium oxide 213, alumina and urease 214 and ZrP 215. The urease is adsorbed onto the alumina in order to immobilize the urease. In any embodiment of the first, second, or third aspects of the invention, the urease can be placed in a sorbent cartridge in a separate layer prior to the alumina (not shown). During priming of the sorbent cartridge, the urease will be dissolved by the water and contact the alumina where urease will be adsorbed and immobilized. The particular order of sorbent layers is not critical to the invention. Any order of sorbent materials within the first compartment 210 is contemplated by the first, second, or third aspects of the invention. For example, in any embodiment of the first, second, or third aspects of the invention, first compartment 210 can contain activated carbon, then hydrous zirconium oxide, then alumina and urease and then ZrP. In any embodiment of the first, second, or third aspects of the invention, the first compartment 210 can contain activated carbon, then alumina and urease, then ZrP, and then hydrous zirconium oxide. Further, the sorbent materials within the first compartment 210 can be intermixed, as opposed to being arranged in layers. After leaving the first compartment 210, fluid is directed by ammonia detector 216 positioned after ZrP reserve module 211. In normal operation, valve 217 is set so as to direct fluid into bypass line 218, and around the reserve line 219 and ZrP reserve module 211. When ammonia detector 216 detects the presence of ammonia or ammonium ions in the fluid leaving first compartment 210, the valve 217 can be switched to direct flow into the reserve line 219 and ZrP reserve module 211. Rechargers (not shown) can optionally be attached to either or both compartments as described above to facilitate recharging the sorbent materials.

Figure 3:
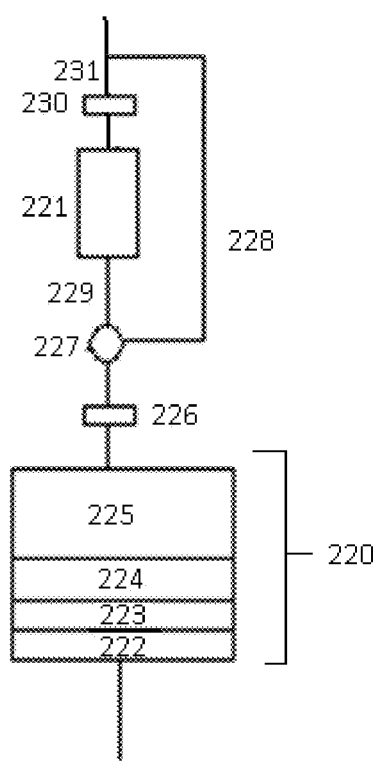
FIG. 3 shows a sorbent cartridge with activated carbon, alumina, urease, hydrous zirconium oxide and zirconium phosphate in the first compartment and a zirconium phosphate reserve compartment with two ammonia detectors.

In any embodiment of the first, second, or third aspects of the invention, a first ammonia detector may be placed in a flow path to only detect ammonia levels in fluid exiting the first ZrP module, and a second ammonia detector may be placed in a flow path to detect ammonia levels in fluid exiting the ZrP reserve as shown in FIG. 3. However, any combination and placement of sensors is contemplated by the first, second, or third aspects of the invention. For safety reasons, ammonia breakthrough can be detected from effluent flow from a primary and/or a secondary reserve utilizing a sensor located in the effluent flow or by utilizing multiple sensors. In particular, fluid leaving the first compartment 220, which can contain activated carbon 222, hydrous zirconium oxide 223, alumina and urease 224 and ZrP 225 in any order or intermixed, can pass by first ammonia detector 226. In normal operation, a valve 227 can direct fluid into bypass line 228 and around ZrP reserve compartment 221. If ammonia is detected by ammonia detector 226 in an unsafe level, valve 227 can be switched to direct fluid into the reserve line 229 and ZrP reserve compartment 221. Fluid leaving the ZrP reserve compartment 221 can pass by second ammonia detector 230. If ammonia is detected leaving the ZrP reserve compartment 221 in unsafe levels, then the system may automatically shut down, thus preventing ammonia from being returned to the patient. In any embodiment of the first, second, or third aspects of the invention, a single ammonia detector can be positioned to detect ammonia in dialysate leaving both the first and second compartments, such as by positioning the ammonia detector after the junction of bypass connector 228, which bypasses the ZrP reserve compartment 221, and connector 231, through which fluid leaving the ZrP reserve compartment 221 can flow.

Figure 4:
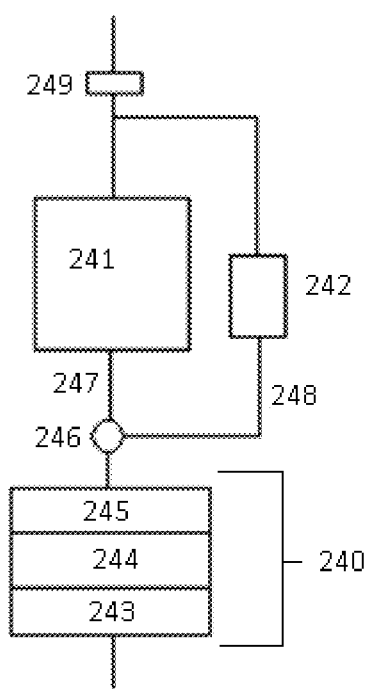
FIG. 4 shows a sorbent cartridge with activated carbon, alumina, urease and hydrous zirconium oxide in a first compartment, zirconium phosphate in a second compartment, and a zirconium phosphate reserve compartment parallel to the second compartment.

In any embodiment of the first, second, or third aspects of the invention, as shown in FIG. 4, the ZrP compartment 241 and the ZrP reserve 242 can be constructed parallel to each other. Fluid exiting a first compartment 240 of a sorbent cartridge can pass by a valve 246. The first compartment 240 can contain activated carbon layer 243, alumina and urease layer 244, and hydrous zirconium oxide layer 245. The particular order of sorbent materials within the first compartment 240 is not critical to the invention. For example, in any embodiment of the first, second, or third aspects of the invention, the first compartment 240 may contain activated carbon, then hydrous zirconium oxide, and then alumina and urease. In any embodiment of the first, second, or third aspects of the invention, the first compartment 240 can contain alumina and urease, followed by hydrous zirconium oxide, and then activated carbon. Further, the first compartment 240 can contain hydrous zirconium oxide, followed by alumina and urease and then activated carbon. In any embodiment of the first, second, or third aspects of the invention, the sorbent materials within the first compartment can be intermixed. In normal operation, the valve 246 can be set so as to direct fluid into ZrP connector 247, and then into ZrP compartment 241. Fluid exiting ZrP compartment 241 can then pass by ammonia detector 249. If ammonia is detected by ammonia detector 249 in a concentration higher than a safe value, the valve 246 can be switched such that fluid is instead directed towards reserve line 248 and ZrP reserve compartment 242.

Figure 5:
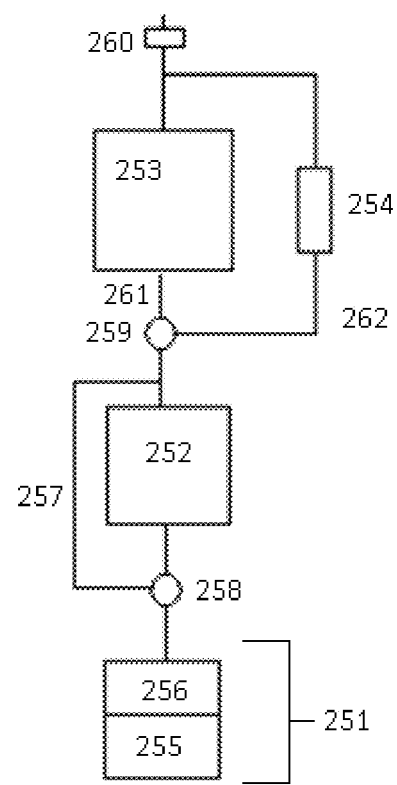
FIG. 5 shows a sorbent cartridge with activated carbon and hydrous zirconium oxide in a first compartment, alumina and urease in a second compartment, zirconium phosphate in a third compartment, a zirconium phosphate reserve compartment parallel to the third compartment and a bypass line to bypass the second compartment.

In any embodiment of the first, second, or third aspects of the invention, as shown in FIG. 5, a second bypass line 257 may be utilized. A first compartment 251 can contain activated carbon 255 and hydrous zirconium oxide 256, in any order or intermixed. A second compartment 252 can contain alumina and urease. A third compartment 253 can contain ZrP. During normal operation, valve 259 can direct fluid from the second compartment 252 through the ZrP connector 261 into the ZrP compartment 253. Fluid leaving ZrP compartment can pass by ammonia detector 260. If ammonia detector 260 detects ammonia or ammonium ions in an unsafe concentration, valve 259 can be switched so that fluid instead passes into reserve connector 262 and ZrP reserve compartment 254. Ammonia detector 260 can also detect ammonia in fluid leaving ZrP reserve compartment 254. The bypass line 257 can bypass the second compartment 252 containing alumina and urease. Thus, when the capacity of the ZrP in both the normal ZrP compartment 253 and the ZrP reserve compartment 254 is exceeded, spent dialysate can pass through compartment 251 containing activated carbon and hydrous zirconium oxide, and valve 258 can then be switched to direct the fluid into the bypass line 257. By bypassing second compartment 252, urea is not converted into ammonia. In this way, once the capacities of both the normal ZrP compartment 253 and ZrP reserve compartment 254 have been exceeded, dialysis can continue, albeit without conversion of urea to ammonia and subsequent removal thereof.

Figure 6:
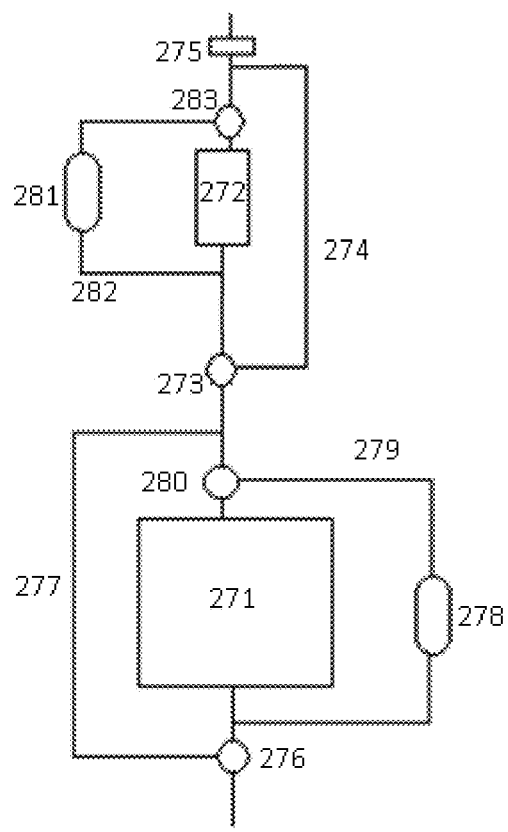
FIG. 6 shows a sorbent cartridge with a zirconium phosphate compartment and a zirconium phosphate reserve compartment with rechargers attached to both compartments.

In any embodiment of the first, second, or third aspects of the invention, one or more rechargers can be attached to the system as shown in FIG. 6 to allow for in-line recharging of the ZrP compartment. In normal operation, fluid will travel through normal ZrP compartment 271. Valve 273 will then direct the fluid into bypass line 274, and around the ZrP reserve compartment 272. When the capacity of the normal ZrP compartment 271 is exceeded, as detected by ammonia detector 275, valve 273 can be switched to direct the spent dialysate to flow to ZrP reserve compartment 272. At the same time valve 276 can be switched, directing fluid into bypass line 277 and around normal ZrP compartment 271. When the spent dialysate is directed to the ZrP reserve 272, the system can also circulate fluid from the recharger 278 through wash line 279 to the normal ZrP compartment 271, recharging the ZrP compartment 271. The fluid leaving normal ZrP compartment 271 can then pass by valve 280, where fluid can be directed either away from normal ZrP compartment 271, or back to recharger 278. In any embodiment of the first, second, or third aspects of the invention, the recharging process can happen automatically when fluid is directed to the ZrP reserve 272. In any embodiment of the first, second, or third aspects of the invention, the user can cause the recharging of the ZrP compartment 271 at any time when dialysate is not actively flowing through the compartment. In any embodiment of the first, second, or third aspects of the invention, a second recharger 281, second wash line 282 and valve 283 can be utilized to recharge the ZrP reserve compartment 272. In any embodiment of the first, second, or third aspects of the invention, another compartment (not shown) containing other sorbent materials, such as activated carbon, alumina and urease and hydrous zirconium oxide can be positioned in the flow path before ZrP compartment 271. In any embodiment of the first, second, or third aspects of the invention, once the system has used the ZrP reserve compartment 272, the system can automatically recharge the reserve compartment 272 when dialysis is complete. This will put the ZrP reserve compartment 272 back into a usable state for the next time the ammonia capacity of normal ZrP compartment 271 is exceeded. In any embodiment of the first, second, or third aspects of the invention, the user can direct the recharging of the ZrP reserve compartment 272 at any time. In any embodiment of the first, second, or third aspects of the invention, the ZrP reserve compartment 272 can be disposable, and can be replaced after a dialysis session that required use of the compartment. In any embodiment of the first, second, or third aspects of the invention, the ZrP reserve compartment 272 can be detached from the rest of the system and sent out for recharging and/or refilling of the ZrP.

In any embodiment of the first, second, or third aspects of the invention, other rechargers can be utilized in the system. The activated carbon, hydrous zirconium oxide and alumina and urease sorbent materials can also be recharged as explained above. In line recharging of compartments containing activated carbon, hydrous zirconium oxide and/or alumina and urease can be accomplished by connecting a recharger to the compartments containing these particular sorbents.

Figure 7:
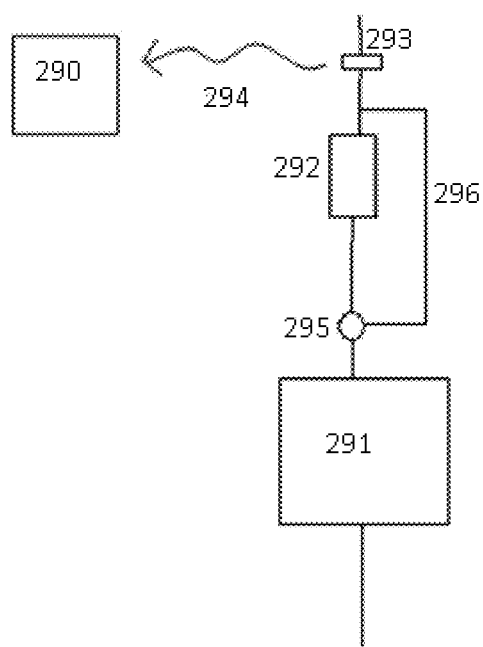
FIG. 7 shows a control system to control the valves in a sorbent cartridge with a zirconium phosphate compartment and zirconium phosphate reserve compartment.

Control system 290, as shown in FIG. 7, can receive data from the ammonia detector 293 via signal 294. When ammonia detector 293 detects an increase in the ammonia or ammonium ion content of the dialysate leaving the normal ZrP compartment 291, a signal 294 can be sent to the control system 290. The signal 294 from the ammonia detector 293 can be communicated either wirelessly or through wired communication. In normal operation, valve 295 can direct fluid into bypass line 296 and around the ZrP reserve compartment 292. In response to a signal 294 showing an increase in ammonia or ammonium ion content of spent dialysate, the control system 290 can automatically switch valve 295. This action will direct spent dialysate into the ZrP reserve compartment 292. In any embodiment of the first, second, or third aspects of the invention, the control system 290 can determine the remaining time scheduled for the dialysis session. If the dialysis session is nearing an end, the control system 290 can automatically shut down the dialysis session. For example, the control system 290 can be set to shut down the system if ammonia breakthrough occurs when there is less than 30 minutes left in a dialysis session.

In any embodiment of the first, second, or third aspects of the invention, an automatic ammonia detector is not used. Instead, the user of the dialysis system can be prompted to determine the ammonia concentration of the dialysate exiting the sorbent cartridge at various times during the session, such as by drawing off a small amount of dialysate and dipping an indicator strip into the fluid. If the indicator strip shows a level of ammonia in the dialysate higher than a predetermined level, the user can manually input the information into the controller so that the controller can switch to the ZrP reserve.

In any embodiment of the first, second, or third aspects of the invention, when ammonia is detected above a predetermined level, and the control system switches flow to the ZrP reserve compartment, an audible or visual signal can be emitted. This signal can inform the user that the capacity of the normal ZrP compartment has been exceeded, and that the system is now utilizing the ZrP reserve compartment. The user is thus notified that after dialysis is complete the ZrP reserve must be replaced or recharged. In any embodiment of the first, second, or third aspects of the invention, the system can prevent the starting of a new session until the ZrP reserve has been replaced or recharged.

Figure 8:
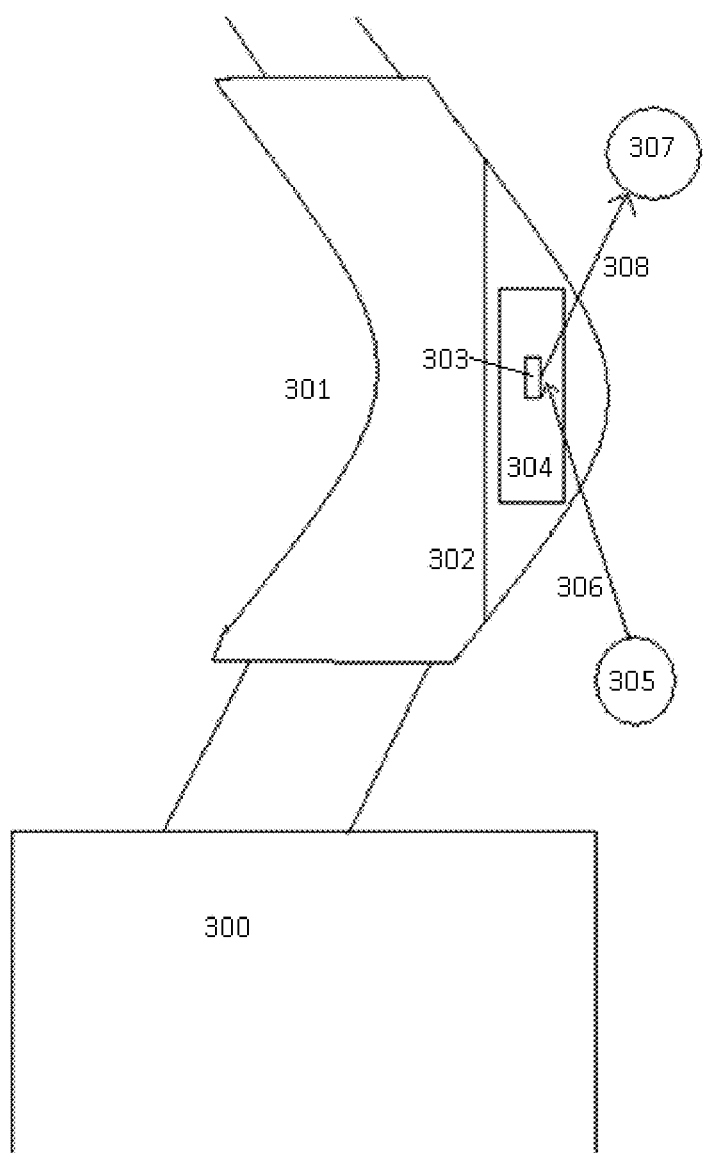
FIG. 8 shows an ammonia detector comprising a chemical sensor behind a liquid impermeable and gas permeable membrane.

Several methods of ammonia detection are known in the art. One non-limiting example is shown in FIG. 8. As dialysate exits the sorbent compartment 300, the dialysate enters the ammonia detector 301. The fluid is directed past a gas permeable and liquid impermeable membrane 302. Ammonia gas diffusing across the membrane 302 can contact chemical sensor 303. The chemical sensor 303 can provide a detectable change when the sensor reacts with ammonia gas. A non-limiting example of a chemical sensor can be a mixture of bromocresol green and malonic acid. The sensor will change color from yellow to blue when exposed to gaseous ammonia. The mixture of bromocresol green and malonic acid can be supported by a suitable substrate such as cellulose paper. Other chemical sensors are contemplated by the invention, and any sensor capable of detecting a change when the sensor is exposed to ammonia known to those of skill in the art is within the invention. A transparent lens 304 covering the chemical sensor 303 can allow light to pass both to and from the chemical sensor 303. The lens 304 can be attached to the ammonia detection system by a clear adhesive, or by insertion into the housing of the device. A light source 305 can shine light 306 through the lens 304 to contact the chemical sensor 303. Suitable light sources can include LEDs. A photodetector 307 can detect the light 308 that is reflected by the chemical sensor 303, and determine whether the change expected when the chemical sensor 303 is exposed to ammonia gas has or is occurring. The photodetector 307 can be any device capable of determining the change due to exposure of chemical sensor 303 when exposed to ammonia, and can include such devices as light sensitive diodes or phototransistors. In any embodiment of the first, second, or third aspects of the invention, no photodetector may be used, and the user may determine whether the requisite color change has occurred.

Figure 9:
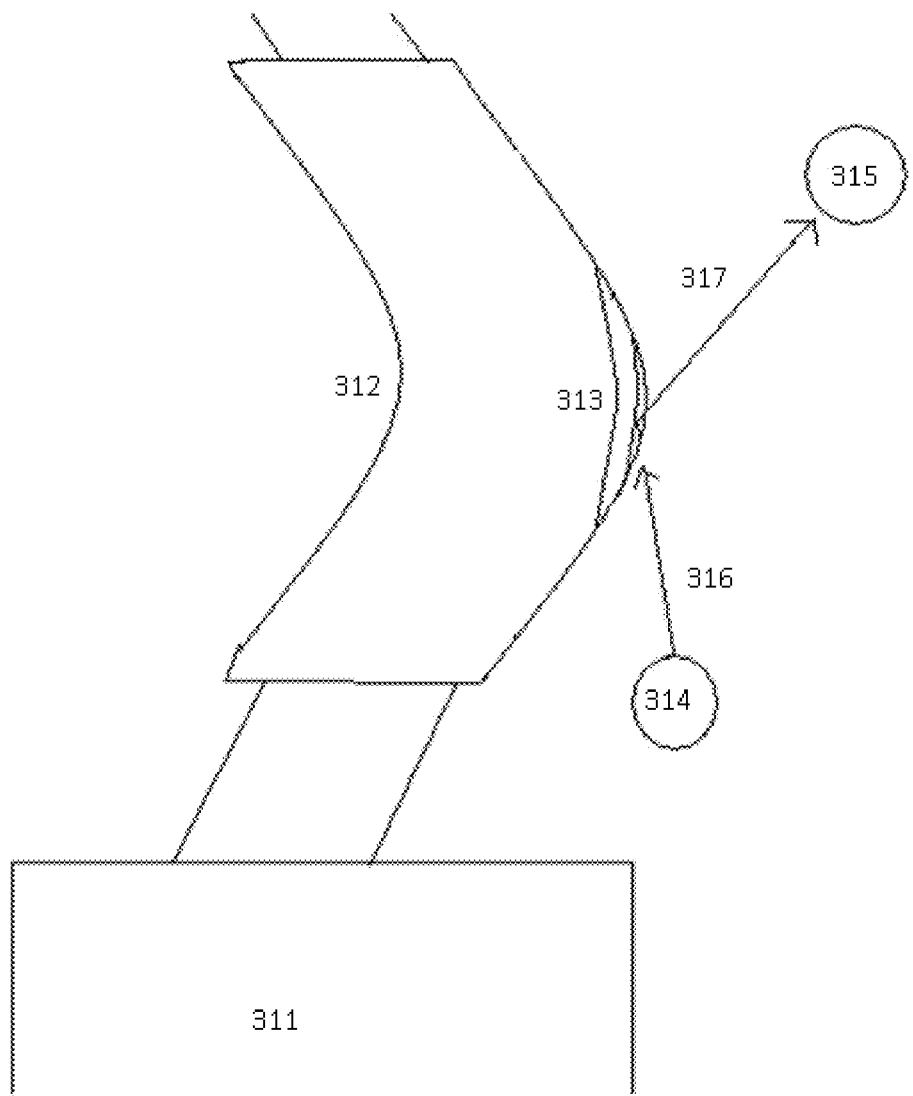
FIG. 9 shows an ammonia detector comprising a hydrophobic membrane with pH sensitive dye embedded therein.

In any embodiment of the first, second, or third aspects of the invention, an ammonia detector as shown in FIG. 9 can be used. The ammonia detector 312 comprises a hydrophobic membrane 313 that is placed in the fluid flow path such that the membrane 313 comes into contact with the spent dialysate after the spent dialysate leaves the sorbent cartridge 311. The hydrophobic membrane 313 can have a microporous structure and a pH sensitive dye embedded in the microporous structure. Ammonia gas can diffuse through the hydrophobic membrane 313. In the presence of gaseous ammonia, the pH sensitive dye embedded in the hydrophobic membrane 313 can change color. A light source 314 can shine light 316 at the membrane 313. The change in color can be detected by a photodetector 315 that can detect light 317 reflected by the membrane 313. The hydrophobic membrane 313 can be constructed from any suitable material known in the art, including but not limited to polypropylene, polytetrafluoroethylene, polyvinylidene difluoride, fluorinated ethylene propylene polymers, acrylic-based fluorinate polymers or copolymers or any other suitable material known in the art. The pH sensitive dye can be bromothymol blue, methyl yellow, methyl orange, 2,4-dinitrophenol, 2,6-dinitrophenol, phenol red, bromophenol blue, combinations thereof, or any other dye known in the art that can undergo a detectable change when exposed to ammonia.

Figure 10:
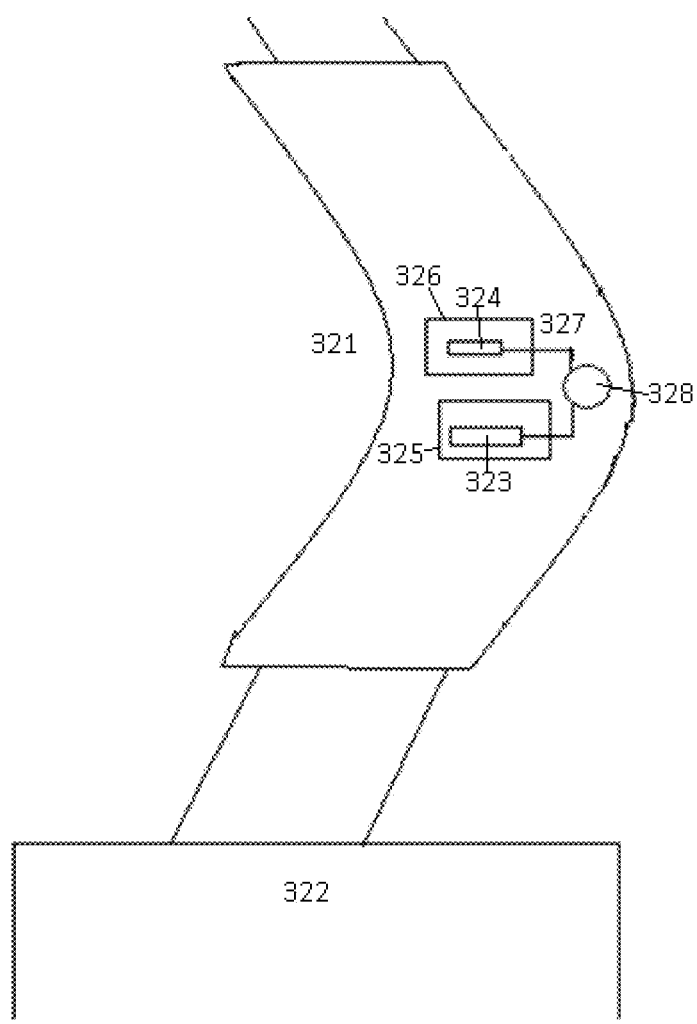
FIG. 10 shows an ammonia detector comprising an ammonium selective electrode.

In any embodiment of the first, second, or third aspects of the invention, the ammonia detector can be an ammonium selective electrode, as shown in FIG. 10. The ammonia detector 321 utilizes an ammonium selective electrode. The ammonium selective electrode comprises a working electrode 323 and a reference electrode 324. An ammonium selective membrane 325 is provided around the working electrode 323. The reference electrode 324 is surrounded by an impermeable membrane 326 with a known ion concentration inside. Ammonium ions from the dialysate leaving the sorbent compartment 322 can pass through the ammonium selective membrane 325 so that the ammonium concentration around the working electrode 323 is the same as the ammonium concentration in the dialysate. The two electrodes 323 and 324 can be connected by an electrical connection 327 and a voltmeter 328. A change in the electric potential between the working electrode 323 and reference electrode 324 is therefore due to a change in the concentration of ammonia in the dialysate. The degree of the change in the electric potential between the two electrodes 323 and 324 is dependent on the concentration of ammonium ions in the dialysate.

The amount of material in the ZrP reserve compartment is flexible. In any embodiment of the first, second, or third aspects of the invention, the ZrP reserve can contain between 50 and 500 g of ZrP. In any embodiment of the first, second, or third aspects of the invention, a larger or smaller ZrP reserve can be used. In any embodiment of the first, second, or third aspects of the invention, the ZrP reserve compartment can contain between 100 and 1500 grams of ZrP.

Sorbent dialysis allows for dialysis with a small volume of dialysate, creating many advantages. In sorbent dialysis, spent dialysate, containing toxins removed from the blood of the patient, is passed through a sorbent cartridge. The sorbent cartridge of the invention can contain sorbent materials that selectively remove specific toxins from the spent dialysate, either completely or by replacing them with non-toxic material. This process converts the spent dialysate into clean dialysate, which is then redirected back to the dialyzer.

Modular sorbent cartridges, wherein each compartment contains select sorbent materials, can be useful in sorbent dialysis. This modular design critically allows for certain portions of the sorbent cartridge to be discarded, refilled, recycled or recharged. In any embodiment of the first, second, or third aspects of the invention, the sorbent materials can be structured into layers and/or intermixed. In particular, the modules can have the sorbent materials either intermixed or in layers wherein any combination of intermixed and layered modules can be used interchangeably together.

To save costs and waste, the modules of the modular sorbent cartridge may be rechargeable. The sorbent cartridges can be reusable or non-reusable, unless specifically specified as reusable. The sorbent material within the module can be recharged and made reusable by passing a solution containing the proper solutes through the layers of the sorbent module.

Figure 11:
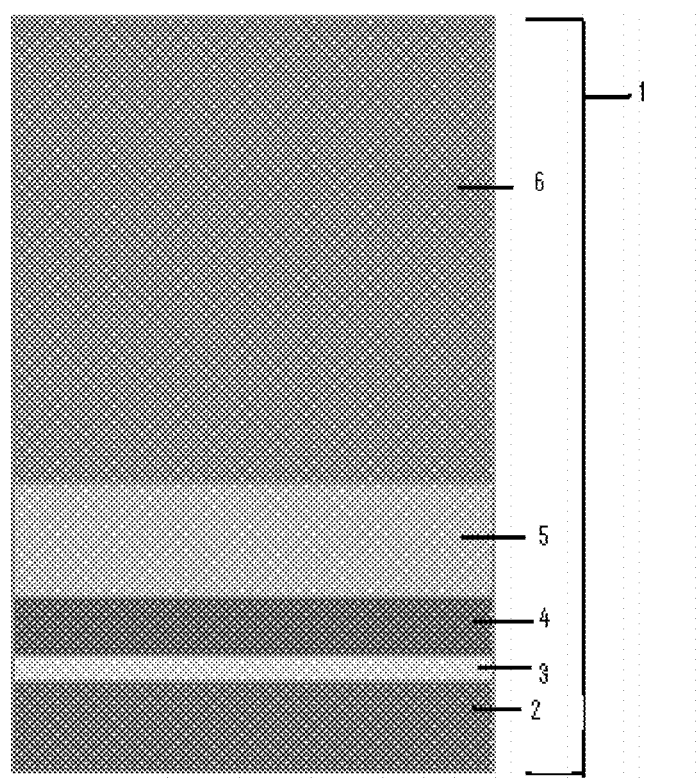
FIG. 11 shows a sorbent cartridge containing activated carbon, hydrous zirconium oxide, urease, alumina, and zirconium phosphate.

One non-limiting exemplary sorbent cartridge is shown in FIG. 11. Spent dialysate or fluid can flow from the bottom of the sorbent cartridge 1 to the top of the cartridge. The first sorbent material the spent dialysate or fluid contacts can be activated carbon 2. Activated carbon 2 will remove nonionic toxins from the fluid by adsorption. Creatinine, glucose, uric acid, 132-microglobulin and other non-ionic toxins, except urea, can be adsorbed onto the activated carbon, removing those toxins from the fluid. Other non-ionic toxins will also be removed by the activated carbon. The dialysate or fluid then continues through the sorbent cartridge 1 to the hydrous zirconium oxide layer 3. The hydrous zirconium oxide layer 3 can remove phosphate and fluoride anions, exchanging them for acetate anions. The fluid can continue to move through the sorbent cartridge 1 into the alumina and urease layer 4. Urease can catalyze the reaction of urea to form ammonia and carbon dioxide. The result of this is the formation of ammonium carbonate. The phosphate anions present in the fluid can also be exchanged for hydroxide ions on the alumina. As the fluid continues through the sorbent cartridge 1, the fluid reaches alumina layer 5. The alumina layer 5 can remove any remaining phosphate ions from the fluid and help retain urease within the sorbent cartridge 1, and in certain configurations this layer can exchange urea for ammonium and other components. The last layer through which the fluid travels can be the ZrP layer 6. In the ZrP layer 6, ammonium, calcium, potassium and magnesium cations can be exchanged for sodium and hydrogen cations. Ammonium, calcium, potassium and magnesium ions all preferentially bind to the ZrP, releasing the hydrogen and sodium ions originally present in the ZrP layer 6. The ratio of sodium to hydrogen ions released depends on the ratio originally present in the ZrP layer 6, and is therefore controllable. The result of the fluid passing through the sorbent cartridge 1 is that the fluid can be regenerated and form clean dialysate that can be safely passed back through a dialyzer to a patient. In any embodiment of the first, second, or third aspects of the invention, potassium, calcium, and magnesium can be added to the clean dialysate to replace any ions which were removed by the sorbent cartridge. The ions can be added and/or controlled via an infusate system (not shown) that can be positioned on a section of the fluid flow path after the sorbent cartridge.

Figure 12:
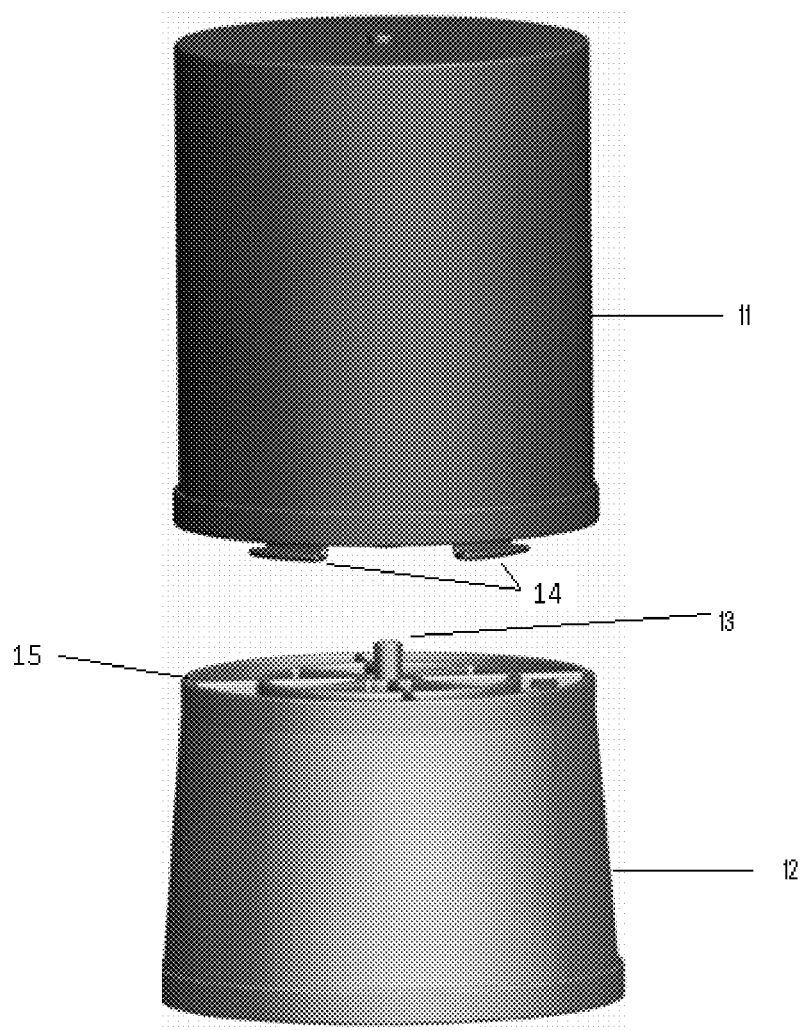
FIG. 12 shows a modular sorbent cartridge with two modules.

Given the cost of the sorbent cartridges and sorbent materials, it is advantageous if parts of the cartridge can be reused or recharged by separating them into modules as described above. As shown in FIG. 12, a reusable module 11 can be fluidly attached to a non-reusable module 12 by a connector 13 with the use of latches 14 disposed near the circumference of the bottom surface of the reusable module 11. The latches 14 can be integrally formed as part of the reusable module 11, or non-reusable module 12. Alternatively, the latches 14 may be a separate component (not shown) that must be attached to the module 11. The latch members 14 can be mated to an annular connection ring 15 disposed on the circumference of the top surface of module 12. One or more engagement members (not shown) can be disposed inside the annular connection ring 15 to engage the latches 14 when positioned relative to each other using a radial motion. Such engagement can cause a rigid connection between the reusable module 11 and the non-reusable module 12. Other known locking or fastening mechanisms known to those of ordinary skill that can effectuate rapid and effective connections between two components are contemplated by the invention. Although only cylindrical modules are shown, it will be understood that modules of any shape such as rectangular, conical, triangular, etc. are contemplated by the first, second, or third aspects of the invention with a corresponding fastening mechanism. In any embodiment of the first, second, or third aspects of the invention, the connector 13 can be formed as part of the reusable module 11 and non-reusable module 12 and need not be a separate component that must be attached to the module 12. Rather, the connector 13 can be molded as part of the reusable module 11 and non-reusable module 12. The connector can be a combination of female and male connectors (not shown) on a module. For example, a female connector can be disposed on one module, and a male connector on the other module, to form one connector (not shown). In any embodiment of the first, second, or third aspects of the invention, the connector can be affixed by mechanical means, glued or rigidly interfaced to the modules 11 and 12. In any embodiment of the first, second, or third aspects of the invention, the connector 13 allows fluid to flow from the non-reusable module 12, through the connector 13, into the reusable module 11. Alternatively, the connector 13 is not a part of either the non-reusable module 12 or reusable module 11 but can be a separate component such as tubing. It will be understood that the connector 13 is defined in its broadest sense and encompasses any fluid connection between two points.

It will be understood that different combinations of reusable and non-reusable modules can be combined together. In any embodiment of the first, second, or third aspects of the invention, both modules may be reusable or both may be non-reusable. Moreover, any one of the modules can be detachable from each other or from a casing forming the body of the sorbent cartridge. The modules can be standardized components that are interchangeable with other modules and easily assembled. For example, the latches 14 in FIG. 12 allow for a simple, twist-lock fitting between two modules. The twist-lock allows for the modules to be connected to each other by an easy and rapid manual motion not requiring complex maneuvering of the modules. The connection, once made, can be resistant to inadvertent disengagement, but can also be readily disengaged when desired with a similar easy and rapid manual manipulation. For example, a force applied on the outside periphery of the modules near the latch, e.g. squeezing the module, can cause the latch member 14 to disengage from the engagement members. In other examples, the modules can be disengaged by simply rotating the modules relative to each other.

In any embodiment of the first, second, or third aspects of the invention, each module can function as a sorbent cartridge independently. In any embodiment of the first, second, or third aspects of the invention, at least two modules can cooperate together when engaged to each other using, for example, the latches 14 in FIG. 12 and being fluidly connected together to function as a sorbent cartridge. The advantage of such a modular design as described herein is that different sorbent materials can be dispersed between the at least two modules to allow for any particular sorbent or combination of sorbent materials to be detachable from a sorbent cartridge.

In any embodiment of the first, second, or third aspects of the invention, one or more fluid connectors can be arranged between any module of the invention, and one or more such fluid connectors can be provided in any of the configurations described herein. For example, a reusable or non-reusable module can have any number of connectors such as 1, 2, 3, 4, 5, or more. The spacing and distribution of the fluid connectors on the module can be positioned to enable and/or increase flow of fluid between the modules. In one example, the fluid connectors can be spaced equidistant from each other or may be located axially or radially. The sorbent cartridge can also have one or more modules each having any number of fluid connectors. In contrast to known sorbent cartridges having a unitary design in which sorbent materials are arranged in layers without any connectors between such layers, the fluid connectors of the present invention allow for controlled fluid or gas flow to any particular sorbent or combination of sorbent materials. The fluid connectors also allow for any particular sorbent or combination of sorbent materials to be detachable from a sorbent cartridge. For example, a detachable module can be constructed with one or more sorbent materials. The detachable module can then be fluidly connected to the sorbent cartridge by fluid connectors. Such a configuration advantageously allows for separate treatment, recycling, or recharging of the sorbent or combination or mixture of sorbent materials not possible with known sorbent cartridges. In particular, known sorbent cartridges have all the sorbent materials being formed into layers or a plurality of sorbent materials being mixed without connectors in between such layers of one sorbent material, or mixtures of sorbent materials. It will be understood that the fluid connectors of the invention can be critical because the connectors control the order of sorbent materials to which a fluid or gas is exposed, the delivery of fluid or gas to a particular sorbent or combination of sorbent materials, and the flow and rate of flow of a fluid or gas to various sorbent materials, layers of sorbent materials, and combination or mixtures of sorbent material.

In any embodiment of the first, second, or third aspects of the invention, it will be understood that the present invention contemplates at least two modules that fit together, which is distinct from known dialysis systems having separate housings that do not form a unitary sorbent cartridge for ready attachment or insertion into a dialysis machine. A unitary sorbent cartridge of the present invention contains one or more of the sorbent materials described herein. In any embodiment of the first, second, or third aspects of the invention, the cation and anion exchange materials necessarily reside in the sorbent cartridge. In other words, the cation and anion exchange resins (or other sorbent materials) are not separated into different housings outside a sorbent cartridge. Although the individual sorbent materials of the present invention may be separated into different detachable and/or reusable modules within the single sorbent cartridge wherein each module is connected by fluid connectors, the single sorbent cartridge design provides reduced size and weight that is not possible with the known dialysis systems having separate housings. The modules, as described herein, can also be further rigidly fixed to each other by latches and engagement members or any fixing or fastening mechanism known to those of ordinary skill in the art. Notably, the sorbent cartridge of the present invention can have all of the sorbent materials described herein including cation and anion exchange resins within a single unitary sorbent cartridge for convenient removal, service and monitoring. In particular, the sorbent cartridge can have a single compartmental design wherein all sorbent materials necessary for performing dialysis are contained within a single compartment. The sorbent cartridge can also have a modular design wherein the sorbent materials are dispersed across at least two different modules, which can be connected to form a unitary body. Once the at least two modules are connected together, the connected modules can form a sorbent cartridge to be fitted to a device or mechanism. Advantageously, the present sorbent cartridge can therefore be easier to recycle, recharge, dispose of, service and remove from a dialysis machine. In any embodiment of the first, second, or third aspects of the invention, the unitary design can also provide for a compact design that can be used in a portable dialysis machine. Further, manufacturability is benefited by the unitary design.

In any embodiment of the first, second, or third aspects of the invention, the fluid connector can be a quick-connect, twist-lock fitting, push-on fitting, or threaded fitting. Other forms of such connection known to those of ordinary skill in the art are also contemplated by the first, second, or third aspects of the invention. Additionally, the connector can comprise a length of tubing and a valve or a valve assembly. In any embodiment of the first, second, or third aspects of the invention, the connector can be manually assembled to connect any component or assembly of the invention. The connector can also be used to rigidly connect any one of the modules to a recharger as defined herein when a separate fastening mechanism is not provided.

It will be understood that the connector provides for a fluid connection in its broadest sense and can include any type of tubing, fluid or gas passageway, or conduit between any one or more components of the invention.

Figure 13:
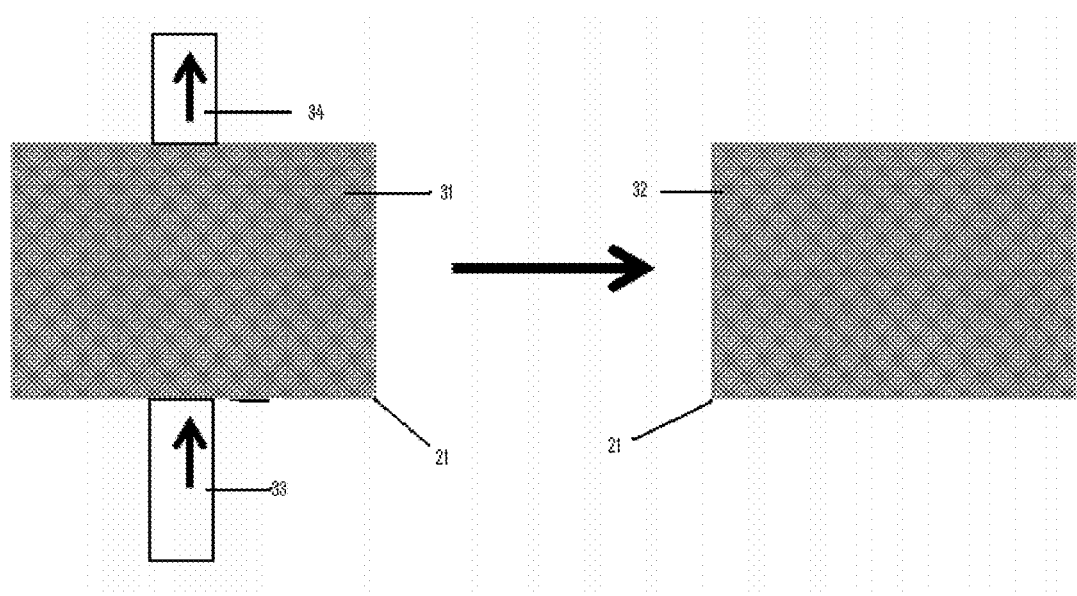
FIG. 13 shows a method for recharging the zirconium phosphate sorbent material.

A method of recharging the ZrP module is shown in FIG. 13. Wash fluid 33, containing sodium and hydrogen ions, can be passed through the reusable module 21, containing the used ZrP 31 with bound ammonium ions. This causes an exchange of ions, wherein hydrogen and sodium ions can replace the ammonium ions on the ZrP 31. The waste fluid 34 exiting the module 21 thus contains the freed ammonium ions, with excess sodium and hydrogen ions. This process creates a recharged ZrP layer 32, containing sodium and hydrogen ions for a subsequent dialysis. In any embodiment of the first, second, or third aspects of the invention, a recharger can be used to recharge spent sorbent material wherein the recharger contains fluid capable of restoring spent sorbent material to, or near, its original state or usable capacity.

Figure 14:
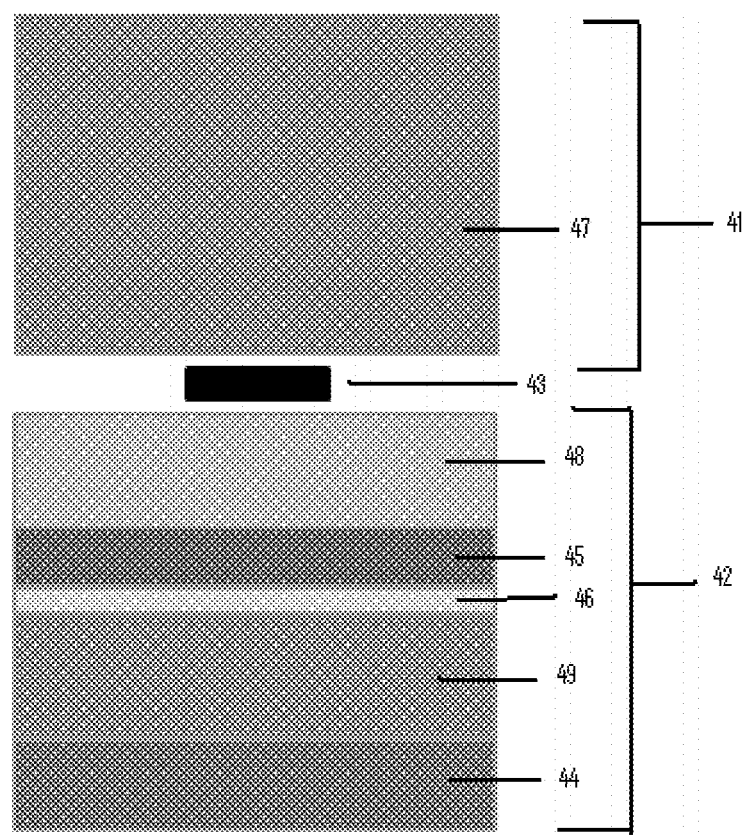
FIG. 14 shows a modular sorbent cartridge with two modules including activated carbon, zirconium phosphate, urease, alumina, and hydrous zirconium oxide in the first module, which can be a reusable module and zirconium phosphate in the second module, which can be a reusable module.

Because calcium and magnesium ions may be more difficult to remove from the ZrP, and therefore the ZrP may be more difficult to recharge, it may be advantageous to remove the calcium and magnesium ions in the first, non-reusable module, so that none of those ions need to be removed in the reusable ZrP module. Such an embodiment of the first, second, or third aspects of the invention is depicted in FIG. 14. Spent dialysate enters the first, non-reusable module 42 where the spent dialysate can first flow through a layer of activated carbon 44 to remove non-ionic uremic toxins. The spent dialysate can then enter into a first layer of ZrP 49. The ZrP layer 49 can remove the calcium, magnesium and potassium from the fluid. Next the fluid can enter the hydrous zirconium oxide layer 46, which can remove the phosphate anions and exchange them with acetate anions. The fluid can then enter the urease layer 45 and alumina layer 48, where the urea can be converted to ammonium carbonate and any remaining phosphate ions can be removed. In any embodiment of the non-reusable module of the first, second, or third aspects of the invention, any arrangement of the activated carbon, ZrP, hydrous zirconium oxide layer, and urease and alumina layer is contemplated. For example, the dialysate can first flow through a first layer of ZrP, activated carbon, then the hydrous zirconium oxide layer, and then enter the urease layer and alumina layer. Alternatively, in any embodiment of the first, second, or third aspects of the invention, the dialysate can first flow through the hydrous zirconium oxide layer, then a first layer of ZrP, then activated carbon, then enter the urease layer and alumina layer. Still further, in any embodiment of the first, second, or third aspects of the invention, the dialysate can first flow through the urease layer and alumina layer, then the hydrous zirconium oxide layer, then a first layer of ZrP, and then the activated carbon. The fluid can then flow through the connector 43, and into the second, reusable, sorbent module 41. The second sorbent module 41 can contain ZrP 47. ZrP layer 47 can exchange the ammonium ions for sodium and hydrogen. Because the calcium, magnesium and potassium ions have already been removed by the first ZrP layer 49, this second layer 47 will not pick up those ions. After dialysis, the second module 41 will only contain ZrP bound to ammonium ions. As such, the sorbent material may be easier to recharge.

In any embodiment of the first, second, or third aspects of the invention, where the reusable module contains ZrP and ion-exchange resin, or ZrP and hydrous zirconium oxide, the module may be recharged in the same manner. The activated carbon layer of a reusable module may be recharged by passing a heated water solution through the activated carbon layer. The alumina and urease layers can be recharged by first passing heated water, or the solutions described above for recharging ZrP, through the layer, and then passing a solution containing urease through alumina and urease layers.

Figure 15:
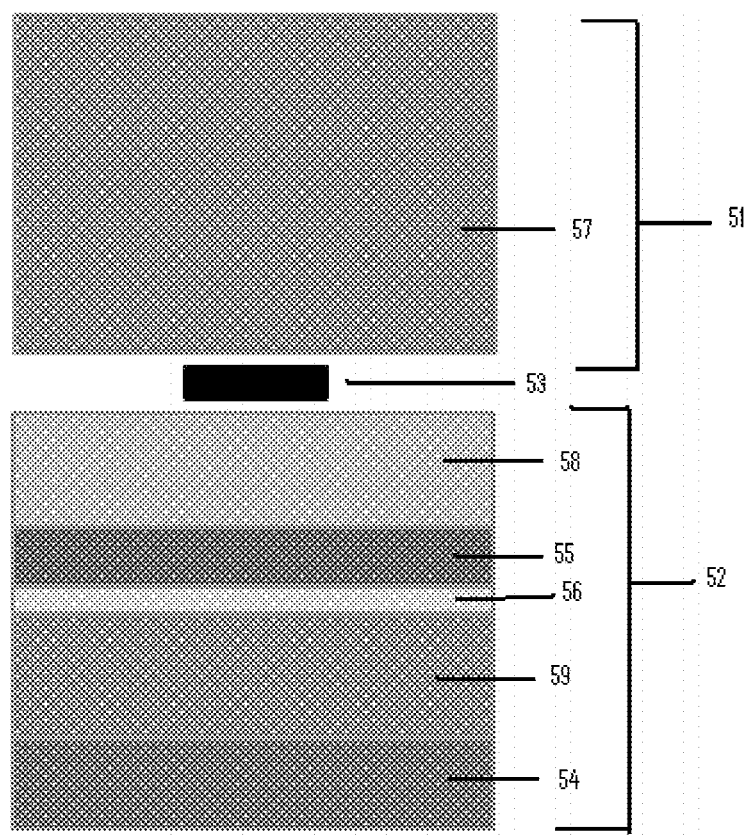
FIG. 15 shows a modular sorbent cartridge with two modules including activated carbon, ion exchange resin, alumina, urease, and hydrous zirconium oxide in the first module, which can be a reusable module, and zirconium phosphate in the second module, which can be a reusable module.

In any embodiment of the first, second, or third aspects of the invention, the sorbent cartridge can be arranged as shown in FIG. 15. Spent dialysate can enter the first, non-reusable, module 52 where the spent dialysate first flows through a layer of activated carbon 54 to remove non-ionic uremic toxins. The spent dialysate then enters into a layer of ion exchange resin 59. The ion-exchange resin layer 59 removes the calcium, magnesium and potassium from the fluid. Next the spent dialysate can enter the hydrous zirconium oxide layer 56, which removes the phosphate anions and exchanges them with acetate anions. The spent dialysate then enters the urease layer 55 and alumina layer 58, where the urea is converted to ammonium carbonate and any remaining phosphate ions are removed. In any embodiment of the first, non-reusable module 52 of the first, second, or third aspects of the invention, any arrangement of the activated carbon, ion exchange resin, hydrous zirconium oxide layer, and urease and alumina layer is contemplated. For example, the dialysate can first flow through an ion exchange resin, activated carbon, then the hydrous zirconium oxide layer, and then enter the urease layer and alumina layer. Alternatively, in any embodiment of the first, second, or third aspects of the invention, the dialysate can first flow through the hydrous zirconium oxide layer, then the ion exchange resin, then activated carbon, then enter the urease layer and alumina layer. Still further, in any embodiment of the first, second, or third aspects of the invention, the dialysate can first flow through the urease layer and alumina layer, then the hydrous zirconium oxide layer, then the ion exchange resin, and then the activated carbon. The fluid can then flow through the connector 53, and into the second, reusable sorbent module 51. The sorbent module 51 contains ZrP 57. The ZrP layer 57 can exchange the ammonium ions for sodium and hydrogen. Because the calcium, magnesium and potassium ions have already been removed by the ion-exchange resin layer 59, the ZrP layer 57 will not pick up those ions. Alternatively, in any embodiment of the first, second, or third aspects of the invention, the ion-exchange resin 59 may be selected to only remove the calcium and magnesium ions, such as by using a chelating ion exchange resin. This will allow use of less of the ion exchange resin. If such a resin is used, the potassium will be removed by the ZrP layer 57. Potassium is easier to remove from ZrP than calcium or magnesium. In any embodiment of the first, second, or third aspects of the invention, the sorbent materials in each module may be intermixed as opposed to being arranged in layers.

One skilled in the art will recognize that different combinations of sorbent materials in both the reusable and non-reusable modules of the sorbent cartridge can be used without being beyond the scope of this invention. The sorbent materials described herein can be mixed together in any combination as shown in the specific embodiments of the invention.

Figure 16:
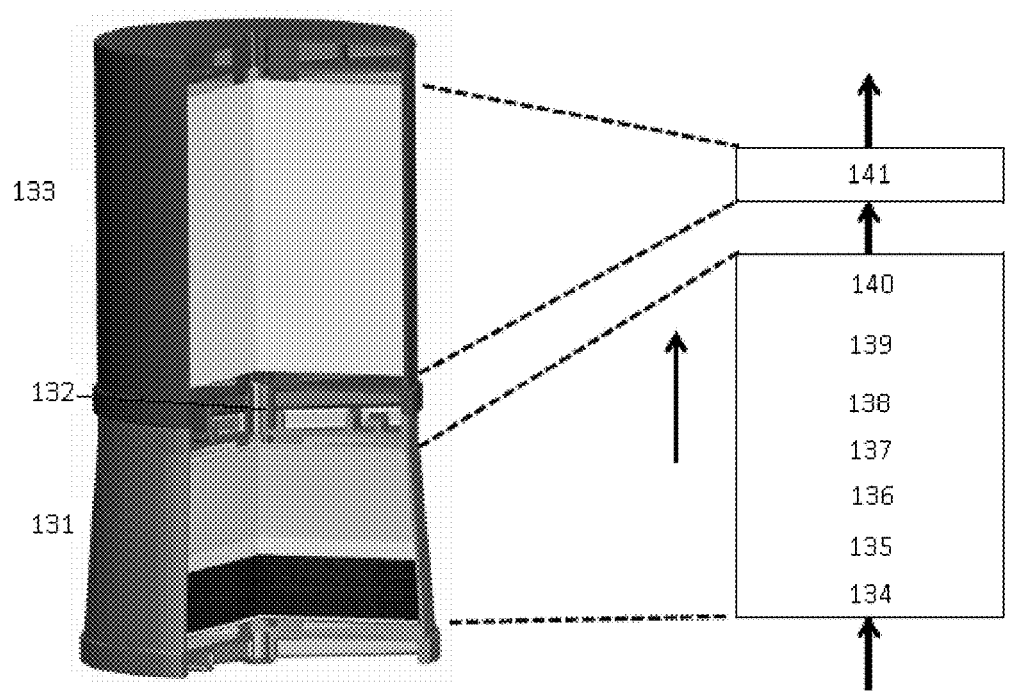
FIG. 16 shows a modular sorbent cartridge with two modules including sodium chloride/sodium bicarbonate, activated carbon, ion exchange resin, active jack bean meal (JBM)/alumina, alumina, hydrous zirconium oxide/glass beads, and sodium chloride in the first module, which can be a reusable module, and zirconium phosphate in the second module.

In any embodiment of the first, second, or third aspects of the invention, the sorbent cartridge can be arranged as shown in FIG. 16. A layer of sodium chloride and sodium bicarbonate 134 are disposed in the first module 131. In any embodiment of the first, second, or third aspects of the invention, the first module 131 can be reusable as defined herein. The sodium chloride and sodium bicarbonate will be dissolved as liquid enters the first module 131. The spent dialysate can then enter a layer of activated carbon 135 to remove non-ionic uremic toxins. The spent dialysate can then enter into a layer of ion-exchange resin 136. In any embodiment of the first, second, or third aspects of the invention, this can be a chelating ion exchange resin to selectively remove calcium and magnesium. The dialysate can then enter a layer of alumina and urease 137, where the urea is converted to ammonium carbonate and phosphate ions are removed. In any embodiment of the first, second, or third aspects of the invention, the urease can be in the form of urease active jack bean meal (JBM). The spent dialysate can next enter a layer of alumina 138. The fluid can then pass through a layer of hydrous zirconium oxide 139. In any embodiment of the first, second, or third aspects of the invention, the hydrous zirconium oxide can be mixed with glass beads. A layer of sodium chloride 140 can be disposed at the end of first module 131, which will be dissolved by the fluid as the fluid passes through the first module 131. The fluid then passes out of the first module 131, through the connector 132, and into the second module 133. In any embodiment of the first module 131 of the first, second, or third aspects of the invention, any arrangement of activated carbon, alumina, urease, ion exchange resin and hydrous zirconium oxide can be used. For example, the fluid can first pass through a layer of sodium chloride and sodium bicarbonate, then activated carbon, then hydrous zirconium oxide, then ion-exchange resin, then alumina and urease and then the sodium chloride. Alternatively, in any embodiment of the first, second, or third aspects of the invention, the fluid can first pass through a layer of sodium chloride, then ion-exchange resin, then activated carbon, then hydrous zirconium oxide, then alumina and urease, and then sodium chloride. The second module 133 can contain ZrP 141, to remove the ammonium ions from solution. In any embodiment of the first, second, or third aspects of the invention, the ZrP 141 can be mixed with glass beads.

One skilled in the art will realize that embodiments of the first, second, or third aspects of the invention can be included that involve the sorbent materials being mixed within the module, as opposed to arranging the materials in layers. Such mixing of the sorbent materials can be performed by interspersing the sorbent materials in a single layer by any method known to those of skill in the art.

Figure 17:
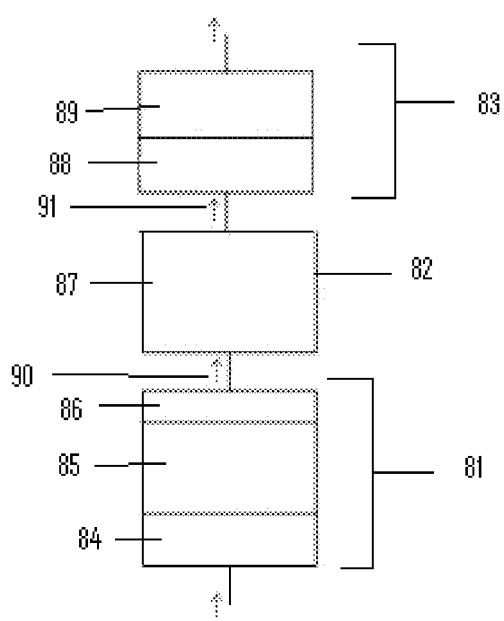
FIG. 17 shows a modular sorbent cartridge with three modules including activated carbon, alumina, urease, and hydrous zirconium oxide in the first module, which can be a reusable module, zirconium phosphate in the second module, and zirconium phosphate and activated carbon in the third module.

The modular sorbent cartridges in this invention are not limited to having two modules. Any number of modules may be utilized in the first, second, or third aspects of the invention. A three module sorbent cartridge is shown in FIG. 17. The first module 81 contains a layer of activated carbon 84, a layer of alumina and urease 85, and a layer of hydrous zirconium oxide 86. In any embodiment of the first, second, or third aspects of the invention, any one of the first module 81, second module 82 or third module 83 can be reusable as defined herein. The described layers can also be mixed together rather than being provided in layers. In any embodiment of the first module 81 of a three module sorbent cartridge of the first, second, or third aspects of the invention, any arrangement of the activated carbon, hydrous zirconium oxide layer, and urease and alumina layer is contemplated. For example, the dialysate can first flow through activated carbon, then the hydrous zirconium oxide layer, and then enter the urease layer and alumina layer. Alternatively, in any embodiment of the first, second, or third aspects of the invention, the dialysate can first flow through the hydrous zirconium oxide layer, then the activated carbon, then enter the urease layer and alumina layer. Still further, the dialysate can first flow through the urease layer and alumina layer, then the hydrous zirconium oxide layer, and then the activated carbon. Again, the described arrangements include not just layers, but also intermixed sorbent materials. The fluid, after passing through these layers, can pass through a first connector 90, and into the second module 82. This second module 82 contains ZrP 87. The fluid can then pass through a second connector 91, and enter a third module 83. This third module 83 contains a second layer of ZrP 88, and a second layer of activated carbon 89 for final purification before passing out of the sorbent cartridge. In any embodiment of the third module 83 of a three module sorbent cartridge of the first, second, or third aspects of the invention, any arrangement of the activated carbon and the second layer of ZrP are contemplated. For example, the dialysate can first flow through activated carbon and then the second layer of ZrP. It will be understood that any number of modules can be configured in the present invention. For example, a sorbent cartridge having four, five, six, seven, or more modules is contemplated by the invention. It will be understood that the described arrangements include not just layers, but also the sorbent materials being intermixed.

As each layer of sorbent material within the modular sorbent cartridge may be recharged, a cartridge is possible where all of the modules are reusable. It is still advantageous to utilize separate modules for the sorbent materials in order to direct the correct recharging solution through the correct module, and because different sorbent materials may need to be replaced more often than others.

To make use of the modular sorbent cartridge easier, the valve assembly may be operated by a programmable controller or computer system that can be programmed to regulate flow through the valves and into and out of the modules. An optical sensor, photocell or other flow sensing apparatus may detect the flow of fluid through any two points in the sorbent cartridge. For example, an optical fluid flow device can be provided for measuring flow wherein the device includes an optical fluid pressure measuring device having sensors positioned in any one of the flow paths between the modules, in the connectors, or in the valve assemblies. Preferably, the sensors will be placed in a passageway defined between the modules. In any embodiment of the first, second, or third aspects of the invention, the optical fluid sensors can be connected to an interferometer associated with an opto-electronic demodulator which has an output signal representing the differential pressure between the two sensed areas. In any embodiment of the first, second, or third aspects of the invention, a flow sensing apparatus can have a flow-responsive element projecting into a fluid flow path, and a position sensor associated with the element which detects a change in position of the flow responsive element in response to the fluid flow. The flow-responsive element can be made of a wide variety of materials having the desired properties known to those of ordinary skill in the art.

Figure 18:
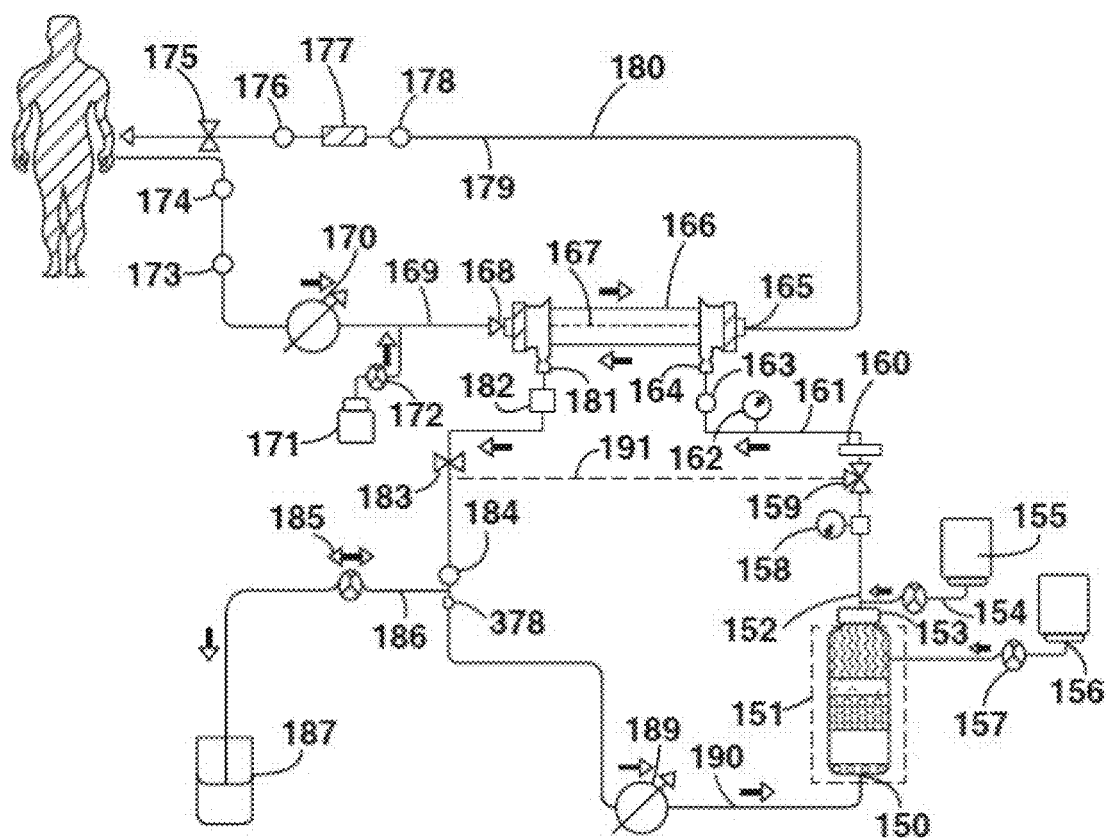
FIG. 18 shows a sorbent cartridge in a controlled compliant dialysis circuit.

In any embodiment of the first, second, or third aspects of the invention, at least one module can be in fluid communication with a controlled compliant dialysis circuit. A non-limiting example of a controlled compliant dialysis circuit is shown in FIG. 18. The patient's blood is circulated through an extracorporeal circuit 180. The portion of the extracorporeal circuit 180 that contains blood drawn from the patient can be referred to as the arterial line 169, which by convention is understood to mean a line for transporting blood from the patient regardless of whether blood is drawn from an artery or vein of the patient. Similarly, the portion that returns blood to the patient can be referred to as the venous line 179. In any embodiment of the first, second, or third aspects of the invention, the arterial line 169 and the venous line 179 connect with one or more veins of the patient. Locomotive power for moving the blood through the extracorporeal circuit 180 is provided by a blood pump 170, which is typically located along the arterial line 169. Blood is typically conveyed through the extracorporeal circuit 180 at a rate of 50 to 600 mL/min and can be adjusted by a controller to any required rate suitable for a procedure performed by the invention. Blood pump 170 can be a peristaltic pump, although those skilled in the art will readily understand that other types of pumps can be used including diaphragm pumps, centrifugal pumps, and shuttle pumps. In any embodiment of the first, second, or third aspects of the invention, the blood pump 170 conveys blood through the dialyzer 166 where the blood is contacted with a blood side of a high permeability dialysis membrane 167. Blood enters the dialyzer 166 through a blood inlet 168 and exits through a blood outlet 165. The pressure of the blood prior to the blood pump 170 is measured by a pressure meter 173 and post dialyzer 166 by a pressure meter 178. The pressure at pressure meter 173 provides an indication of the adequacy of the blood flow into the circuit where increased vacuum is an indication of a less adequate access flow. The pressure indication at pressure meter 178 can serve to detect obstructions in the venous bloodline. An air trap 177 is placed along the extracorporeal circuit 180 to prevent the introduction of air into the circulatory system of the patient. The air trap 177 is not limited to a particular design. Typical air traps employ a hydrophobic membrane that allows air to be separated from an air-liquid mixture by allowing air to pass through the membrane and retaining water-based fluids. Alternatively the air trap 177 can be run full, where a pressure meter can use a flexible impermeable membrane to transmit pressure pulses to a pressure transducer such that there is no direct air-blood interface. Air-fluid detectors 174 and 176 are present to confirm that air is not present in the extracorporeal circuit 180. Air fluid detectors 174 and 176 can be ultrasonic sensors that can detect a change in solution density or scattering due to the presence of air or air bubbles.

During the course of conveyance of blood along the extracorporeal circuit 180, heparin or another anticoagulant is added to the blood to prevent clotting of blood within the dialyzer 166 or blood conveyance pathway/extracorporeal circuit 180. Heparin or another anticoagulant is added from an anticoagulant container 171 at a metered rate using an anticoagulant pump 172. The anticoagulant pump 172 can be any pump capable of accurately metering heparin.

Dialysate within the system is conveyed through one of a first dialysate pathway 161 in the dialysate circuit, which carries dialysate to the dialyzer 166, or a second bypass pathway 191 shown in a dashed line, which serves to bypass the dialyzer 166. The first and second pathways 161 and 191 have one or more conduits for conveying the dialysate. Access to the second bypass pathway 191 is controlled by valve 159. It is understood by one skilled in the art that three-way valve 159 can be replaced with a two-way valve or four-way valve with the same result to control the flow through the dialyzer 166 or bypass pathway 191. The first dialysate pathway 161, the second bypass pathway 191, and residual volume in the dialyzer 166 including conduits for conveying the dialysate together form a dialysis circuit 190 that houses the circulating volume of the dialysate present in the system.

Dialysate that is conveyed through the dialyzer 166 on the dialysate side of the dialysis membrane 167 picks up waste products from the blood, including urea, by diffusion, hemofiltration or hemodiafiltration. Dialysate enters the dialyzer 166 at a dialysate inlet end 164 and exits at an outlet end 181. The dialysate exiting the dialyzer 166 passes through a blood leak detector 182 that can determine the presence of blood in the dialysate indicating a breach in the dialysis membrane 167. Flow of dialysate from the dialyzer 166 can be stopped or controlled through the operation of valve 183 as well as to prevent the backup of dialysate into the dialyzer 166. The dialysate is conveyed through a sorbent cartridge 151 to remove waste products before being re-conveyed through the dialyzer 166. The dialysate enters the sorbent cartridge 151 at a dialysate inlet end 150 and exits at an outlet end 152. An air trap 153 can be positioned before or after outlet end 152 to remove gasses introduced into the dialysate by the sorbent cartridge 151. The volume of actively circulating dialysate is determined by the total void volume of the conduits and the sorbent cartridge 151 forming the dialysis circuit 190. The void volumes of the conduits and of the sorbent cartridge 151 forming the dialysis circuit 190 have a non-expandable or substantially inflexible volume.

The total void volume of the conduits having a substantially inflexible volume prevents the passive inflow and outflow of fluid volume due to pressure changes that can occur over the course of treatment. This results in a benefit because not all of the pressure changes during treatment are under precise control by a user or operator. A controlled compliance dialysis circuit is achieved by actively controlling the inflow (influx) and outflow (efflux) of fluid to and from the dialysis circuit 190 and the extracorporeal circuit 180. In this manner, the volume of fluid crossing the dialysate membrane 167 is under direct control and can be accurately determined.

The controlled compliance dialysis circuit can be accurately controlled to precisely remove or add fluid to the dialysis circuit. Due to the substantially inflexible void volume of the conduits, the sorbent cartridge 151 and other components of the dialysis circuit 190, the net movement of fluid over any time interval across the dialysate membrane can be accurately controlled by creating a means to accurately introduce or remove fluid from the patient. This capability is used to enhance the convective clearance of the system while controlling the net fluid removed from the patient.

As shown in FIG. 18, the dialysate is moved along the dialysis circuit 190 by a dialysate pump 189. When the control pump 185 is not operating, fluid along the length of the dialysis circuit 190 flows at a rate determined by the dialysate pump 189. When the control pump 185 is operating, fluid exiting the dialyzer 166 and traveling toward the conduit 186 is flowing at a rate that is the combination of the rates of the control pump 185 and the dialysate pump 189. However, the fluid traveling from the entry point of conduit 186 into the dialysis circuit 190 to the dialyzer 166 is traveling at the rate of the dialysate pump 189. As such, the rate of fluid traveling to the dialyzer 166 is not affected by the operation of the control pump 185. The dialysate pump 189 can be operated at a rate from about 10 to about 400 mL/min, the specific rate being dependent on the rate of the blood pump 170 at the desired contact time with the dialysis membrane 167 to achieve diffusion of impurities from blood to the dialysate. The rate of the dialysate pump 189 and the blood pump 170 can be controlled by a controller (not shown).

Due to the substantially inflexible void volume of the conduits and the sorbent cartridge 151, bulk fluid or water is prevented from moving across the membrane 167 from the extracorporeal circuit 180 of the dialyzer 166 to the dialysate circuit 190 of the dialyzer 166. Specifically, due to the controlled compliant feature of the void volume of the dialysis circuit 190, water cannot passively move from the extracorporeal side to the dialysate side through the dialysis membrane 167. In the event of factors that tend to increase pressure on the extracorporeal side of the dialysis membrane 167, such as increased blood flow rate or blood viscosity, pressure across the membrane will automatically be equalized due to the limited volume of the dialysis circuit 190 and the non-compressible nature of the dialysate. In the event of factors that tend to increase pressure on the dialysate side of the dialysis membrane 167, such as increased dialysis flow rate, net movement of water from the dialysis circuit 190 to the extracorporeal circuit 180 is prevented by a vacuum that would form in the dialysis circuit 190 in the event of such a movement. Since the dialyzer can be a high flux type, there is some fluid flux back and forth across the dialyzer membrane 167 due to the pressure differential on the blood and dialysate sides of the membrane. This is a localized phenomenon due to the low pressure required to move solution across the membrane and is called backfiltration, however results in no net fluid gain or loss by the patient.

Using the controlled compliance dialysis circuit described herein, net movement of water across the dialysis membrane 167 occurs under active control rather than passively due to pressure differences that develop across the dialysis membrane 167 due to normal operations. A control pump 185 is present and accesses the controlled compliance dialysis circuit 190 through a conduit 186. In any embodiment of the first, second, or third aspects of the invention, the conduit 186 joins with the controlled compliance dialysis circuit 190 at a point downstream from the dialyzer 166. The control pump 185 can be operated in an influx direction that moves fluid from a control reservoir 187 to the controlled compliance dialysis circuit 190 or in an efflux direction that moves fluid from the controlled compliance dialysis circuit 190 into the control reservoir 187. Due to the substantially inflexible volume of the dialysis circuit 190, volume added to the controlled compliance dialysis circuit when the control pump 185 operates in the influx direction causes net movement of fluid from the dialysate side of the dialysis membrane 167 to the extracorporeal side of the dialysis membrane 167. When the control pump 185 is operated in the efflux direction, fluid is drawn from the extracorporeal side of the dialysis membrane 167 into the controlled compliance dialysis circuit. In any embodiment of the first, second, or third aspects of the invention, the control pump 185 can be operated at a rate from 0 to about 500 mL/min in either direction.

An infusate pump 154 can be used to add a cation infusate 155 into the hemofiltration circuit 190 to generate a fluid having a proper physiological composition to serve as a replacement fluid for introduction into the extracorporeal circuit 180. A bicarbonate solution in a container 156 can further be added by a pump 157 to maintain a physiological pH in the fluid prior to introduction to the extracorporeal circuit.

One skilled in the art will understand that various combinations and/or modifications and variations can be made in the stacked sorbent assembly depending upon the specific needs for operation. Moreover, features illustrated or described as being part of the invention can be included in the invention, either alone or in combination.

We claim:
1. A dialysate regeneration system comprising:
a material capable of converting urea to ammonia from a dialyzed fluid;

a first compartment having at least one sorbent material wherein the at least one sorbent material is capable of removing ammonia or ammonium ions generated from the converted urea from the dialyzed fluid;

a second compartment having at least one sorbent material capable of removing ammonia or ammonium ions generated from the converted urea from the dialyzed fluid;

at least one ammonia detector to detect ammonia breakthrough; wherein one or more valves are responsive to detected ammonia breakthrough;

the first and second compartment in fluid communication with each other as controlled by the one or more valves positioned to selectively direct the fluid into one of the first and second compartments based on detection of ammonia breakthrough from the other one of the first and second compartments.

2. The dialysate regeneration system of claim 1, the at least one ammonia detector positioned in a fluid flow path wherein the ammonia detector detects ammonia or ammonium ions in the fluid after the fluid leaves the first or second compartment.

3. The dialysate regeneration system of claim 2, further comprising a processor configured to receive data from the ammonia detector; wherein the processor automatically either:
  (i) switches the one or more valves to direct flow into the second compartment based on the ammonia detector that detects ammonia or ammonium ions in a higher concentration than a pre-set value; or
  (ii) stops the dialysis system based on the ammonia detector that detects ammonia or ammonium ions in a higher concentration than a pre-set value and there is less than a pre-set amount of time remaining in a dialysis session.

4. The dialysate regeneration system of claim 2 wherein either:
  (i) the at least one ammonia detector is positioned in the fluid flow path wherein the ammonia detector also detects ammonia or ammonium ions in the fluid after the fluid leaving the second compartment; or
  (ii) wherein the dialysate regeneration system further comprises a second ammonia detector positioned in a fluid flow path wherein the second ammonia detector detects ammonia or ammonium ions in the fluid leaving the second compartment.

5. The dialysate regeneration system of claim 1, further comprising one or more additional compartments positioned before or after the first compartment; wherein the one or more additional compartments contain at least one sorbent material.

6. The dialysate regeneration system of claim 5, wherein any one of the additional compartments contains a sorbent material capable of converting urea into ammonia or ammonium ions.

7. The dialysate regeneration system of claim 6, further comprising a bypass line fluidly connected to a second set of one or more valves positioned before the additional compartment such that the fluid is caused to bypass the additional compartment; wherein the second set of one or more valves automatically causes fluid to bypass the additional compartment based on that ammonia or ammonium ions are detected in a concentration higher than a pre-set value in the fluid leaving both the first compartment and the second compartment.

8. The dialysate regeneration system of claim 1, further comprising an alarm mechanism for providing an alert based on the ammonia detector detecting ammonia or ammonium ions in a higher concentration than a pre-set level.

9. The dialysate regeneration system of claim 1 wherein the at least one sorbent material in at least one of the first and second compartment comprises zirconium phosphate.

10. The dialysate regeneration system of claim 9 wherein the second compartment contains between 50 and 500 grams of zirconium phosphate, or between 100 and 1500 grams of zirconium phosphate.

11. The dialysate regeneration system of claim 1, further comprising a recharger fluidly connected to the one or more valves such that fluid is directed from the recharger into either or both of the first compartment and the second compartment.

12. The dialysate regeneration system of claim 1, further comprising a bypass line fluidly connected to the one or more valves such that the one or more valves direct the fluid into the bypass line to bypass either the first or second compartment.

13. The dialysate regeneration system of claim 1, wherein the one or more valves is a single valve positioned to direct the fluid into the second compartment and bypassing the first compartment based on the detection of ammonia breakthrough from one of the first and second compartments.

14. A dialysate regeneration system comprising:
  a sorbent cartridge comprising at least a first compartment and a second compartment positioned in series;
  the first compartment having at least one sorbent material wherein the at least one sorbent material is capable of removing ammonia or ammonium ions from a fluid;
  the second compartment having at least one sorbent material capable of removing ammonia or ammonium ions from the fluid;
  the first and second compartment in fluid communication with each other as controlled by one or more valves positioned on a connector after the first compartment;
  a bypass line connected to the one or more valves positioned on a connector after the first compartment; wherein the one or more valves are initially set to direct the fluid into the bypass line and around the second compartment and wherein the one or more valves are switched to direct the fluid into the second compartment based on detection of ammonia breakthrough from the first compartment; and
  at least one ammonia detector to detect the ammonia breakthrough; wherein the one or more valves are responsive to the detected ammonia breakthrough.

15. The dialysate regeneration system of claim 14, the at least one ammonia detector positioned in a fluid flow path after the first compartment such that the ammonia detector detects ammonia or ammonium ions in fluid leaving the first compartment.

16. The dialysate regeneration system of claim 15, further comprising a processor configured to receive data from the at least one ammonia detector; wherein the processor causes the one or more valves to switch, such that the fluid is directed into the second compartment, when the ammonia detector detects ammonia or ammonium ions in the fluid leaving the first compartment.

17. The dialysate regeneration system of claim 14 wherein the first compartment further comprises a sorbent material capable of converting urea to ammonia or ammonium ions.

18. The dialysate regeneration system of claim 14, further comprising an additional compartment positioned before the first or second compartments wherein the additional compartment comprises at least one sorbent material capable of converting urea to ammonia or ammonium ions.

19. The dialysate regeneration system of claim 14, the one or more valves comprising a first set of valves and a second set of valves, wherein the first set of valves positioned to direct the fluid into the second compartment and the second set of valves positioned to direct the fluid bypassing the first compartment.

20. A method for performing dialysis, comprising:
 determining an amount of ammonia leaving a first compartment capable of removing ammonia or ammonium ions generated from converting urea in a dialyzed fluid from a dialysis fluid using an ammonia sensor;
 diverting flow of the dialysis fluid from the first compartment to a second compartment capable of removing ammonia or ammonium ions from a fluid based on detection of ammonia breakthrough from the first compartment by the ammonia sensor.

21. The method of claim 20, further comprising the step of:
 switching one or more valves to direct the fluid into the second compartment when the ammonia detector detects ammonia or ammonium ions in the dialysis dialyzed fluid leaving the first compartment.

22. The method of claim 20, further comprising the step of:
 bypassing the first compartment using the one or more valves such that the dialysis dialyzed fluid is directed into a bypass line and around the first compartment.

* * * * *